US012611136B2

(12) United States Patent
Alalaiwi et al.

(10) Patent No.: US 12,611,136 B2
(45) Date of Patent: Apr. 28, 2026

(54) EPI-SEIZURE DEVICE FOR THE PREDICTION AND DETECTION OF TONIC-CLONIC SEIZURES

(71) Applicant: Imam Abdulrahman Bin Faisal University, Dammam (SA)

(72) Inventors: Fawzayah Ahmed Alalaiwi, Dammam (SA); Areej Abdulrahman Alyousef, Dammam (SA); Maram Abdualaziz Almansour, Dammam (SA); Munerah Abdulhakim Alsaadi, Dammam (SA); Sarah Ali Alfares, Dammam (SA); Lola El Sahmarany, Dammam (SA); Maha Alshammari, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 497 days.

(21) Appl. No.: 18/350,900

(22) Filed: Jul. 12, 2023

(65) Prior Publication Data

US 2024/0341669 A1     Oct. 17, 2024

Related U.S. Application Data

(60) Provisional application No. 63/495,627, filed on Apr. 12, 2023.

(51) Int. Cl.
*A61B 5/00*          (2006.01)
*A61B 5/0531*       (2021.01)
(Continued)

(52) U.S. Cl.
CPC ............ *A61B 5/4094* (2013.01); *A61B 5/002* (2013.01); *A61B 5/0531* (2013.01);
(Continued)

(58) Field of Classification Search
CPC ..... A61B 5/002; A61B 5/0531; A61B 5/0816; A61B 5/113; A61B 5/4094; A61B 5/4818;
(Continued)

(56) References Cited

U.S. PATENT DOCUMENTS 8,795,173 B2    8/2014 Poh et al.
10,631,760 B2   4/2020 Dracup et al.
(Continued)

OTHER PUBLICATIONS

Böttcher S, Bruno E, et al. ; "Detecting Tonic-Clonic Seizures in Multimodal Biosignal Data From Wearables: Methodology Design and Validation"; JMIR Mhealth, Feb. 2, 2021; vol. 9(11) (Year: 2021).*

(Continued)

*Primary Examiner* — Jon Eric C Morales
(74) *Attorney, Agent, or Firm* — Oblon, McClelland, Maier & Neustadt, L.L.P.

(57)          ABSTRACT

A device for predicting and monitoring epileptic seizures includes a wearable electrodermal activity (EDA) sensor that measures skin conductance, a wearable respiration rate (RR) sensor and a microcontroller. The microcontroller receives high-frequency phasic signals from the EDA sensor and compares the phasic signals to a first skin conductance threshold value and a second skin conductance threshold value to determine when to actuate a warning of an epi-seizure condition of a patient. When a warning alarm is generated, the microcontroller compares a number of breaths per minute to respiration rate thresholds to determine when a patient is in a seizure state. The microcontroller transmits warning and seizure mode alerts to a epi-seizure telemedicine application stored on a smart device to alert a caregiver of an incipient or on-going epileptic seizure.

20 Claims, 29 Drawing Sheets

(51) Int. Cl.
    *A61B 5/08*              (2006.01)
    *A61B 5/113*           (2006.01)

(52) U.S. Cl.
    CPC ............ *A61B 5/0816* (2013.01); *A61B 5/113*
              (2013.01); *A61B 5/4818* (2013.01); *A61B*
              *5/6823* (2013.01); *A61B 5/6826* (2013.01);
              *A61B 5/6831* (2013.01); *A61B 5/7225*
              (2013.01); *A61B 5/7275* (2013.01); *A61B*
              *5/746* (2013.01); *A61B 5/748* (2013.01)

(58) Field of Classification Search
    CPC ... A61B 5/6823; A61B 5/6826; A61B 5/6831;
              A61B 5/7225; A61B 5/7275; A61B
              5/746; A61B 5/748; A61B 5/0533; A61B
                                      5/725
    See application file for complete search history.

(56)                References Cited

U.S. PATENT DOCUMENTS

| | | |
|---|---|---|
| 2012/0083700 A1 | 4/2012 | Osorio |
| 2012/0283526 A1 | 11/2012 | Gommesen et al. |
| 2013/0116514 A1 | 5/2013 | Kroner et al. |
| 2014/0163413 A1 | 6/2014 | Conradsen et al. |
| 2015/0272494 A1 | 10/2015 | Fuerst |
| 2021/0259621 A1* | 8/2021 | Alves ...................... A61B 7/00 |

OTHER PUBLICATIONS

Mike Williams, "Rice has help for people with epilepsy", Current News, https://news2.rice.edu/2013/05/13/rice-has-help-for-people-with-epilepsy/, May 13, 2013, 3 pages.

Areej Alyousef, et al., "Development of Low Cost "Epi-seizure" Device for the Prediction and Detection of Tonic-Clonic Seizures", Youtube, https://www.youtube.com/watch?v=ExV_0p8cjYw, Application ID #: 7414, Apr. 25, 2022, 9 pages.

"ESP32-PICO-MINI-02, ESP32-PICO-MINI-02U Datasheet", Espressif Systems, Version 1.2, 2022, 33 pages.

"James Electronics HC-05: Bluetooth HC-05 Transceiver Module", Jameco Electronics, https://www.jameco.com/z/HC-05-Major-Brands-Bluetooth-HC-05-Transceiver-Module_2297711.html, Part No. 2297711, HTS code: 8543709655, 2002-2023, 3 pages.

* cited by examiner

400

602

604

605

606

608

610

612

EPI-SEIZURE DEVICE FOR THE PREDICTION AND DETECTION OF TONIC-CLONIC SEIZURES

CROSS REFERENCE TO RELATED APPLICATIONS

The present application claims the benefit of priority to U.S. Prov. App. No. 63/495,627, entitled "Development of Low Cost Epi-Seizure Device For The Prediction And Detection Of Tonic-Clonic Seizures", filed on Apr. 12, 2023, and incorporated herein by reference in its entirety.

STATEMENT REGARDING PRIOR DISCLOSURE BY THE INVENTORS

Aspects of the present disclosure are described in Areej AlYousef, et al., "Development of low cost "Epi-seizure" device for the prediction and detection of tonic-clonic seizures" YouTube Apr. 26, 2022, youtube.com/watch?v=ExV_Op8cjYw, which is incorporated herein by reference in its entirety.

STATEMENT OF ACKNOWLEDGEMENT

The inventors acknowledge the financial support provided by the Biomedical Engineering Department, Imam Abdulrahman Bin Faisal University, Dammam, Saudi Arabia.

BACKGROUND

Technical Field

The present disclosure is directed to an epi-seizure device for the prediction and detection of tonic-clonic seizures.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Epilepsy is a neurological disorder in which abnormal brain activity may cause seizures or periods of unusual behavior, sensations, and sometimes loss of awareness. Conventionally, electroencephalography (EEG) signals were used for detecting and analyzing epileptic seizures. However, the analysis of seizures by processing EEG signals has one or more challenges, such as choosing an acceptable range for EEG signal accuracy, proper utilization of EEG signal samples, and selecting specific algorithms for different patients and different types of seizures. Further, in an EEG detection test, electrical activity in the brain is measured using multiple EEG electrodes attached, for example, to the scalp of a patient. Requiring the use of EEG electrodes attached to the scalp causes inconvenience to the patient. Also, acquiring EEG signals is cumbersome and generally requires an expert to apply an EEG device and monitor the EEG signals.

Conventionally, EEG signals have been acquired in a controlled environment such as a clinical laboratory or hospital, at a fixed or at an appointed time. However, the seizures can occur any time, and there may be times when the patient may not be able to receive assistance. There is a need to improve the detection of seizures to improve treatment or to alert caregivers of the patient of a seizure in order to prevent potentially dangerous situations associated with the seizure. Early detection of the disease is critical for preventing symptoms of seizures from occurring.

Epileptic seizures may be categorized into motor seizures and non-motor (absence) seizures. A tonic-clonic seizure is a motor seizure and the most common type seen in patients with epilepsy. A seizure could, for example, result in sudden unexplained death in epilepsy (SUDEP). A possible mechanism causing SUDEP may include tonic activation of the diaphragm muscle to prevent breathing, neurogenic pulmonary edema, asystole, and cardiac dysrhythmia. If a sleeping patient experiences a seizure involving those conditions, and a caregiver is not aware that the seizure is occurring, he may not be able to render timely aid, which can sometimes lead to patient fatality. Therefore, it is required to monitor the patient continuously to ensure timely aid can be provided. It is also important in using minimally intrusive devices to monitor the patient to prevent interference with daily activities and which can be comfortably used.

US2004/0230105A1 describes predicting epileptic seizures using an electromyography (EMG) sensor to detect a biomedical signal connected to a processor that processes the signals using a segmentation algorithm. Various signal readings are then obtained and analyzed in a prediction algorithm using a set of hidden Markov models to predict a seizure. The U.S. publication uses complex and time-consuming processes to detect seizures that may not be suitable for continuous monitoring. Furthermore, the U.S. publication requires the detection of multiple signals at multiple locations and the adjustment of parameters for each individual user.

US20120083700 describes an implantable medical device for detecting an epileptic event based on an autonomic signal and a neurologic signal of a patient. The implantable medical device includes a detection module for receiving an autonomic signal indicative of the patient's autonomic activity and for receiving a neurologic signal indicative of the patient's neurological activity. However, an electrode assembly of the implantable medical device is surgically coupled to the vagus nerve in the patient's neck or at another location, e.g., near the patient's diaphragm or at the esophagus/stomach junction. As a result, the implantable medical device cannot be used as a non-invasive device. Further, the implantable medical device includes several surgical risks during placement or removal, infection, and implant failure.

US 20150272494 describes receives physiologic data to monitor a patient for epileptic seizures. Sensors are held on a wristband and can measure skin conductivity, including subtle electrical changes across the surface of the skin, compare the measurements against thresholds indicating the level of severity of the increase in conductivity, and trigger an alert at certain levels. However, '494 application describes receiving a user's entry/input, where the user's entry/input can be the user's last food intake before going to sleep, stress level, etc. (and not on continuous basis), and therefore is prone to error.

Hence, there is a need for an epi-seizure device for the prediction and detection of tonic-clonic seizures, which is a low-cost, non-invasive, portable device.

SUMMARY

In an embodiment, a device for predicting and monitoring epileptic seizures is described. The device includes a wearable electrodermal activity (EDA) sensor configured to measure skin conductance and generate EDA signals, a wearable respiration rate (RR) sensor configured to measure chest movement and generate respiratory rate signals, an alarm configured to have a warning mode and a seizure alert mode, a second order low pass filter having a cut-off frequency of 0.05 Hz, and a microcontroller. The second order low pass filter is configured to filter the EDA signals to remove low frequency tonic signals having frequencies less than 0.05 Hz and to pass high frequency phasic signals having frequencies greater than 0.05 Hz. The microcontroller is connected to the second order low pass filter and the RR sensor, wherein the microcontroller is configured to receive the high frequency phasic signals, compare an amplitude of the high frequency phasic signals to a first skin conductance threshold value and a second skin conductance threshold value, wherein the first skin conductance threshold is less than the second skin conductance threshold. When the amplitude of the high frequency phasic signals is greater than the first skin conductance threshold value but less than the second skin conductance threshold value, the microcontroller is configured to actuate the alarm in the warning mode. When the amplitude of the high frequency phasic signals is greater than or equal to the second skin conductance threshold value, the microcontroller is configured to receive the respiratory rate signals, calculate a number of breaths per minute based on the respiratory rate signals, and compare the number of breaths per minute to a first respiration rate threshold. When the number of breaths per minute is less than the first respiration rate threshold, the microcontroller is configured to identify an apnea condition of the breathing and actuate the alarm in the seizure alert mode. When the number of breaths per minute is greater than the first respiration rate threshold, the microcontroller is configured to compare the number of breaths per minute to a second respiration rate threshold. When the number of breaths per minute is greater than the second respiration rate threshold, the microcontroller is configured to identify a tachyapnea condition of the breathing and actuate the alarm in the seizure alert mode.

In another exemplary embodiment, a system for predicting and monitoring epileptic seizures is described. The system includes a wearable electrodermal activity (EDA) sensor, a wearable respiration rate (RR) sensor, an alarm, a second order low pass filter, a communications device, a smart device, and a microcontroller. The wearable electrodermal activity (EDA) sensor is configured to measure skin conductance and generate EDA signals. The wearable respiration rate (RR) sensor is configured to measure chest movement and generate respiratory rate signals. The alarm is configured to have a warning mode and a seizure alert mode. The second order low pass filter has a cut-off frequency of 0.05 Hz. The second order low pass filter is configured to filter the EDA signals to remove low frequency tonic signals having frequencies less than 0.05 Hz and to pass high frequency phasic signals having frequencies greater than 0.05 Hz. The smart device is configured with an epi-seizure telemedicine application. The microcontroller connected to the communications device, the EDA sensor and the RR sensor. The microcontroller is configured to receive the high frequency phasic signals and compare an amplitude of the high frequency phasic signals to a first skin conductance threshold value and a second skin conductance threshold value, wherein the first skin conductance threshold is less than the second skin conductance threshold. When the amplitude of the high frequency phasic signals is greater than the first skin conductance threshold value but less than the second skin conductance threshold value, the microcontroller is configured to actuate the alarm in the warning mode. When the amplitude of the high frequency phasic signals is greater than or equal to the second skin conductance threshold value, the microcontroller is configured to receive the respiratory rate signals, calculate a number of breaths per minute based on the respiratory rate signals, and compare the number of breaths per minute to a first respiration rate threshold. When the number of breaths per minute is less than the first respiration rate threshold, the microcontroller is configured to identify an apnea condition of the breathing and actuate the alarm in the seizure alert mode. When the number of breaths per minute is greater than the first respiration rate threshold, the microcontroller is configured to compare the number of breaths per minute to a second respiration rate threshold. When the number of breaths per minute is greater than the second respiration rate threshold, the microcontroller is configured to identify a tachyapnea condition of the breathing and actuate the alarm in the seizure alert mode. The microcontroller is configured to generate a communications packet including the low frequency tonic signals, the high frequency phasic signals, the number of breaths per minute, the warning alert and the seizure alert, and transmit the packet to the smart device configured with the epi-seizure telemedicine application. The epi-seizure application is configured to display any one of the warning alert, the seizure alert, and a prompt to press a stop command on a touchscreen of the smart device.

In another exemplary embodiment, a method of using an epi-seizure device is described. The method includes wrapping a wearable electrodermal activity (EDA) sensor including two nickel electrodes around a hand of a patient so that a first nickel electrode contacts a medial phalange of an index finger, and a second nickel electrode contacts a medial phalange of a middle finger. The method includes securing a wearable chest band including wearable respiration rate sensor around a chest of a patient. The method includes turning on a microcontroller of the wearable respiration rate sensor to start monitoring the patient for the onset of an epileptic seizure. The method includes measuring, by the wearable RR sensor, chest movement of the patient and generating respiratory rate signals. The method includes measuring, by the wearable EDA sensor, skin conductance of the patient and generating EDA signals. The method includes filtering, by a second order low pass filter having a cut-off frequency of 0.05 Hz, the EDA signals to remove low frequency tonic signals having frequencies less than 0.05 Hz and to pass high frequency phasic signals having frequencies greater than 0.05 Hz. The method includes receiving, by the microcontroller, the high frequency phasic signals and the respiratory rate signals. The method includes comparing, by the microcontroller, an amplitude of the high frequency phasic signals to a first skin conductance threshold value and a second skin conductance threshold value. The method includes actuating, by the microcontroller, an alarm in the warning mode when the amplitude of the high frequency phasic signals is greater than the first skin conductance threshold value but less than the second skin conductance threshold value. When the amplitude of the high frequency phasic signals is greater than or equal to the second skin conductance threshold value, the method includes calculating, by the microcontroller, a number of breaths per minute based on the respiratory rate signals. The method includes comparing, by the microcontroller, the number of breaths per minute to a first respiration rate threshold. When the number of breaths per minute is less than the first respiration rate threshold, the method includes identifying, by the microcontroller, an apnea condition of the breathing and actuating the alarm in a seizure alert mode. When the number of breaths per minute is greater than the first respiration rate threshold, the method includes comparing, by the microcontroller, the number of breaths per minute to a second respiration rate threshold. When the number of breaths per minute is greater than the second respiration rate threshold, the method includes identifying, by the microcontroller, a tachyapnea condition of the breathing and actuating the alarm in the seizure alert mode.

The foregoing general description of the illustrative embodiments and the following detailed description thereof are merely exemplary aspects of the teachings of this disclosure, and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1A:
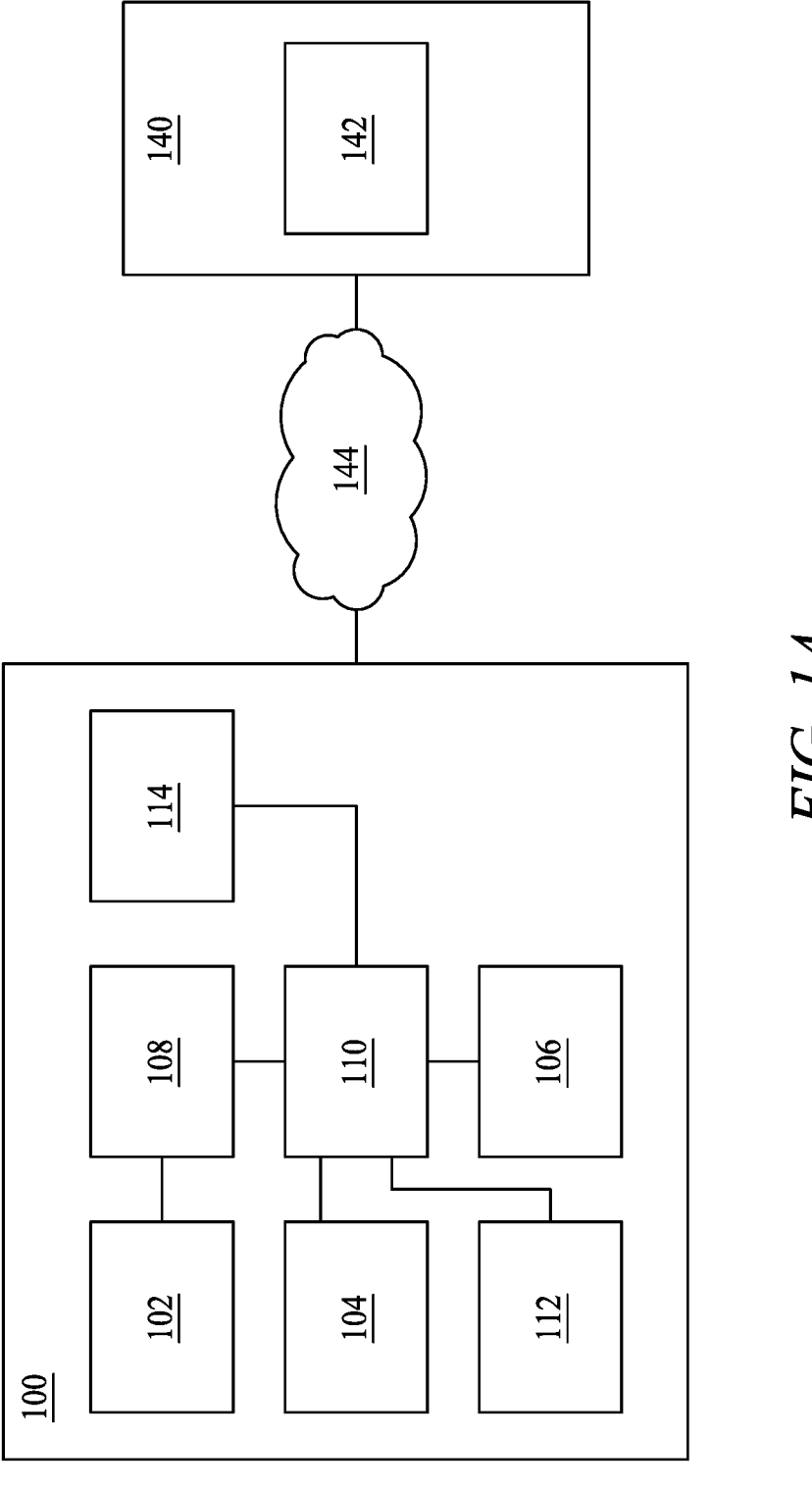
FIG. 1A is a schematic block diagram of a device for predicting and monitoring epileptic seizures, according to certain embodiments.

In the drawings, like reference numerals designate identical or corresponding parts throughout the several views. Further, as used herein, the words "a", "an" and the like generally carry a meaning of "one or more" unless stated otherwise.

Furthermore, the terms "approximately", "approximate", "about" and similar terms generally refer to ranges that include the identified value within a margin of 20%, 10%, or preferably 5%, and any values therebetween.

Epilepsy is a neurological disorder in which brain activity becomes abnormal, causing seizures or periods of unusual behavior, sensations, and sometimes loss of awareness. Unpredictable seizures undoubtedly have an effect on one's lifestyle. Epileptic patients may have limited educational possibilities, inability to get a driver's license, difficulties in getting certain jobs, and limited access to healthcare and life insurance. These limitations to epilepsy patients are due to seizures at can occur anytime. Continuous monitoring and treatment can help epilepsy patients reduce injuries or dangers. Continuous monitoring requires a non-invasive, highly responsive, cost-effective, portable, and predictive device that could benefit early seizure detection. The predictive device should be able to notify a caregiver through a mobile application.

Aspects of this disclosure are directed to a device and system for predicting and monitoring epileptic seizures. The epileptic patient may need support from a caregiver in order to intervene and assist during a seizure. The present disclosure is directed for monitoring patients round the clock and particularly during sleep times, as the patients could experience seizures and incidents, such as sudden unexpected death in epilepsy (SUDEP), especially during sleep if they do not have support. The device (epi-seizure device) of the present disclosure operates in two phases: a prediction phase and a detection phase. In the prediction phase, the device is configured to monitor the preictal stage (a first stage) of the seizure using an electrodermal activity (EDA) sensor. In the detection phase, the ictal and postictal stages of the seizure are monitored via a respiratory rate (RR) sensor and the EDA sensor. The EDA sensor and the RR sensor are configured to work simultaneously. If the device senses any abnormality in the EDA, the device is configured to alert a caregiver through an alarm that a seizure is predicted to occur. Then, if the device detects an irregularity in the RR, the device is configured to alert the caregiver through the alarm that a seizure is currently happening.

In an aspect, the device for predicting and monitoring epileptic seizures includes a wearable electrodermal activity (EDA) sensor that measures skin conductance, a wearable respiration rate (RR) sensor and a microcontroller. The microcontroller receives high-frequency phasic signals from the EDA sensor and compares the phasic signals to a first skin conductance threshold value and a second skin conductance threshold value to determine when to actuate a warning of an epi-seizure condition of a patient. When a warning alarm is generated, the microcontroller compares a number of breaths per minute to respiration rate thresholds to determine when a patient is in a seizure state. The microcontroller transmits warning and seizure mode alerts to an epi-seizure telemedicine application stored on a smart device to alert a caregiver of an incipient or on-going epileptic seizure.

In various aspects of the disclosure, non-limiting definitions of one or more terms that will be used in the document are provided below.

The term "galvanic skin response (GSR)" refers to changes in sweat gland activity that are reflective of the intensity of our emotional state, otherwise known as emotional arousal. The GSR is also known as skin conductance.

The term "apnea condition" refers to a condition in which a breathing rate is lower than a normal breathing rate.

The term "tachyapnea condition" refers to a condition in which a breathing rate is higher than a normal breathing rate. Tachypnea condition refers to rapid breathing. The normal breathing rate for an average adult is 12 to 20 breaths per minute. In children, the number of breaths per minute can be at a higher resting rate than seen in adults.

FIG. 1A-FIG. 1G illustrate a high level configuration of device for predicting and monitoring epileptic seizures.

FIG. 1A illustrates a schematic block diagram of a device 100 for predicting and monitoring the epileptic seizures. The device 100 is a special-purpose device, which is configured to provide an alert service to a caregiver to support an epileptic patient during a seizure or to alert the caregiver that the seizure may be expected in a predefined time. The device 100 is coupled to a data communication network 144. As shown in FIG. 1A, the device 100 is configured to communicate with at least one smart device 140 over the data communication network 144.

The device 100 includes various components such as a wearable electrodermal activity (EDA) sensor 102, a wearable respiration rate (RR) sensor 104, an alarm 106, a second order low pass filter (LPF) 108, a microcontroller 110, a display screen 112, and a communications device 114. In an example, the components of the device 100 may be suitably combined in a single chip or disposed on the same circuit board. In some aspects, the components are implemented on separate chips. Implementations of the device 100 not disclosed are contemplated herein. The at least one smart device 140 includes any one of a computer, a laptop, a mobile communication device, a personal assistant device, a customized device for receiving and processing device, a data processing device and the like.

Figure 1B:
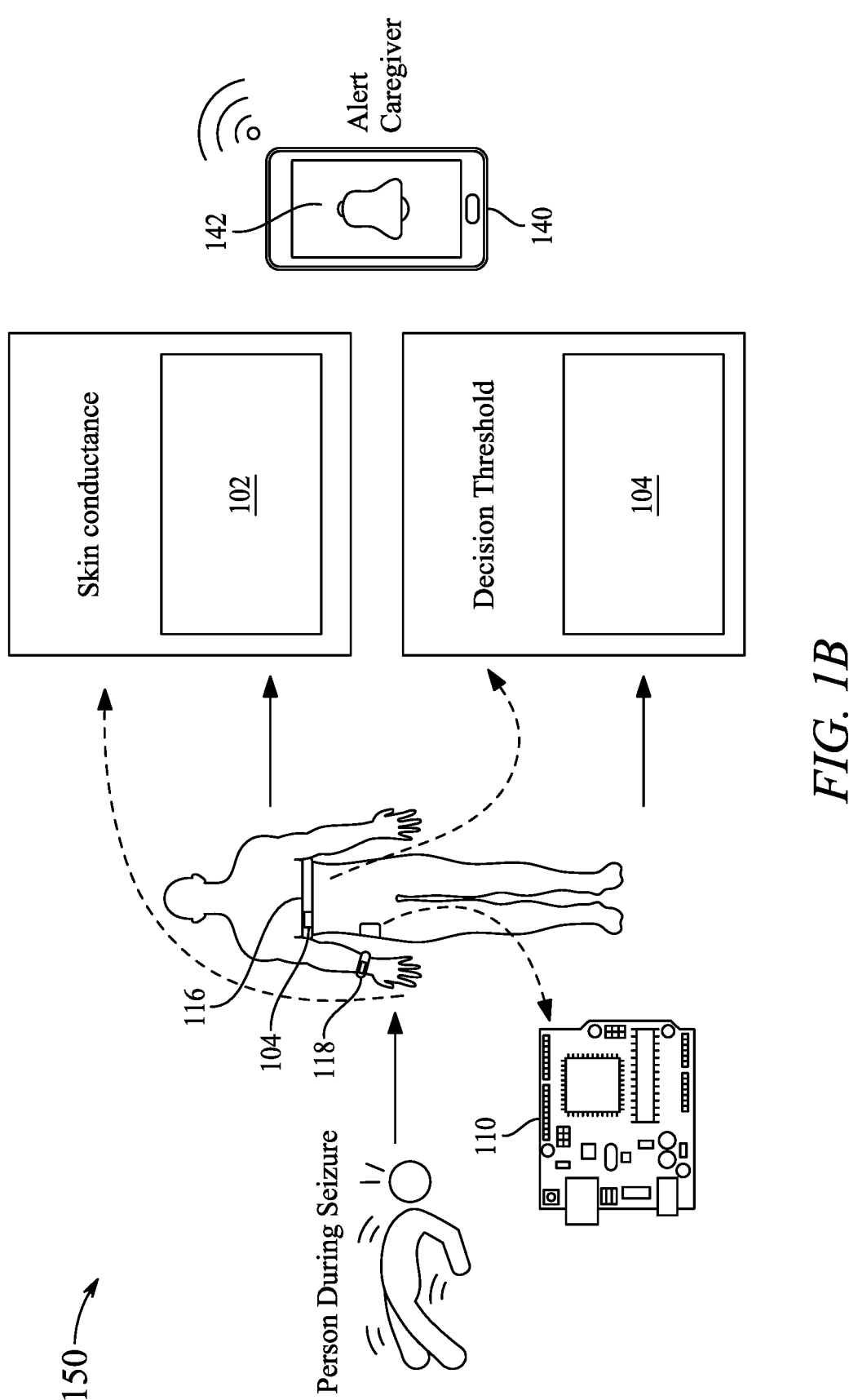
FIG. 1B is an exemplary overview of the device, according to certain embodiments.

FIG. 1B shows an exemplary implementation of the device 100. The device 100 includes a wearable chest band 116. The wearable chest band 116 is configured to secure the wearable RR sensor 104 around the chest of the patient.

The wearable EDA sensor 102 is configured for determining EDA of a human. The EDA is an indication of activation of the nervous system and is considered an indication of emotional arousal or stress. During 'emotional arousal' sweat is secreted, leading to an enhancement in skin impedance or skin conductance. The wearable EDA sensor 102 is configured to measure changes in skin conductance and generate EDA signals. The EDA sensor 102 generates EDA signals by detecting changes in the electrical properties of the skin in response to stress or anxiety or before the epileptic seizure. In an example, the EDA sensor 102 measures electrical properties of the skin by recording the electrical resistance of the skin by passing a low voltage current signal or by recording weak current signals generated by the body. In some examples, the EDA sensor 102 may be placed in a glove, a brace or a hand wrap such that the EDA sensor 102 comes in contact with a set of fingers of a hand. In some examples, the EDA sensor 102 is woven into the glove, the brace or the hand wrap. In an example, an electrode of the glove, the brace or the hand wrap may deliver electrical stimulation through or across glabrous skin surface to a target nerve or tissue within the hand. As shown in the exemplary implementation, the device 100 includes a hand wrap 118 that is configured to secure the EDA sensor 102 around the set of fingers of the patient (as shown in FIG. 1B). The hand wrap 118 includes two nickel electrodes located so as to contact a medial phalange of each of an index finger and a middle finger.

The wearable RR sensor 104 is configured to measure the chest movement of the patient and generate respiratory rate signals. The wearable RR sensor 104 is configured to monitor the respiration rate of the patient. In an exemplary implementation, the wearable RR sensor 104 is placed between a rigid rectangular plate and a rigid outer band. The rigid rectangular plate and the rigid outer band are separated by a fixed distance, forming a space between the rigid rectangular plate and the rigid outer band. In a structural aspect, the wearable RR sensor 104 includes a plurality of motion sensors, placed in the formed space (shown in FIG. 1F). Each motion sensor includes a pneumatic plunger (a pneumatic cylinder or a pneumatic actuator), a conductive plate, and a capacitive sensor. The motion sensor includes the pneumatic plunger, a magnetic plate, and a capacitive sensor. The pneumatic plunger is configured to rise and fall as a breath is inhaled and exhaled, respectively. The conductive plate is attached to the pneumatic plunger. As the respective pneumatic plunger rises and falls, the capacitive sensor is configured to sense changes in an electric field due to a change in the proximity of the conductive plate from a magnetic field sensor or an electric field sensor. For example, the magnetic field sensor or the electric field sensor are fixedly located on the rigid outer band. Each motion sensor is configured to generate the respiratory rate signals in response to the changes in the electric field sensed by the capacitive sensor. The wearable RR sensor 104 is located in or on the wearable chest band 116 (as shown in FIG. 1B). The length of the pneumatic plunger may range from 0.25 cm to 1.5 cm. The length of the pneumatic plunger is selected based on a measured chest circumference of the patient. In an example of an infant from birth to 3 years of age as a patient, the length of the pneumatic plunger may be 0.25 cm. In an example of a child of 3 years to 8 years of age as a patient, the length of the pneumatic plunger may be 0.5 cm. In an example of a child of 8 years to 13 years of age as a patient, the length of the pneumatic plunger may be 1.0 cm. In an example of an adult man or female, the length of the pneumatic plunger may be 1.5 cm.

The second order LPF 108 is operatively connected to the EDA sensor 102 and receives the EDA signals from the EDA sensor 102. In an example, the second order LPF 108 has a cut-off frequency of 0.05 Hz. The second order LPF 108 is configured to filter the EDA signals by removing low frequency tonic signals and generate high frequency phasic signals having frequencies greater than 0.05 Hz. For example, the low frequency tonic signals have frequencies less than 0.05 Hz.

The alarm 106 is configured to generate an alarm signal. The alarm 106 is configured to operate in a warning mode and in a seizure alert mode. In an example, the alarm 106 is a visual alarm and an audio alarm. The visual alarm includes a plurality of LED lights. In an example, a green LED can indicate the warning mode, and a red LED can indicate the seizure alert mode. In an example, the audio alarm includes a speaker. The audio alarm is configured to generate a voice message. In a non-limiting example of the warning mode, the speaker may play a voice message "Pay attention, a seizure is expected." In the seizure alert mode, the speaker may play a voice message "seizure, please help", "call emergency", and the like.

The microcontroller 110 is connected to the second order LPF 108 and the RR sensor 104. The microcontroller 110 is configured to receive the high frequency phasic signals from the second order LPF 108 and the respiratory rate signals from the RR sensor 104, respectively.

The microcontroller 110 includes a memory, a signal processing circuit, and a central processing unit (CPU). The memory is configured to store program instructions. The memory is additionally configured to store preprocessed data. In an aspect, the memory is configured to store a first skin conductance threshold value, a second skin conductance threshold value, a first respiration rate, a record respiration rate, a plurality of media files, etc. The memory may include any computer-readable medium known in the art including, for example, volatile memory, such as Static Random Access Memory (SRAM) and Dynamic Random Access Memory (DRAM) and/or nonvolatile memory, such as Read Only Memory (ROM), erasable programmable ROM, flash memories, hard disks, optical disks, and magnetic tapes.

The signal processing circuit is configured to employ preprocessing on the received data (signal) such as filtration and amplification of the received data. For example, the signal processing circuit includes an analog front end that provides filtration, primarily time domain filtration, and amplification of the received signal.

The CPU is configured to execute the instructions. The CPU is configured to cooperate with the memory to fetch and execute computer-readable program instructions stored in the memory.

The microcontroller 110 is configured to compare an amplitude of the received high frequency phasic signals to the first skin conductance threshold value and the second skin conductance threshold value, fetched from the memory. In an example, the first skin conductance threshold value is 15 μSiemens. In an example, the second skin conductance threshold value is 20 μSiemens. The microcontroller 110 is configured to identify abnormally high sweating indicative of a preictal stage of the epileptic seizure when the high frequency phasic signals are greater than the first skin conductance threshold value of 15 μSiemens and less than the second skin conductance threshold value of 20 μSiemens.

When the amplitude of the received high frequency phasic signals is greater than the first skin conductance threshold value but less than the second skin conductance threshold value (representing the preictal stage), the microcontroller 110 is configured to actuate the alarm 106 in the warning mode.

When the amplitude of the high frequency phasic signals is greater than or equal to the second skin conductance threshold value, the microcontroller 110 is configured to calculate a number of breaths per minute based on the respiratory rate signals.

In an operational aspect, the microcontroller 110 is connected to each of the motion sensors (for example, a Hall sensor) and receives the respiratory rate signals. Each increase and decrease of the respiratory rate signals is representative of one breath taken by the patient. To calculate each breath, the microcontroller 110 divides the received signals by two. The microcontroller 110 calculates the number of breaths per minute by averaging the number of breaths per minute obtained from each motion sensor.

The microcontroller 110 compares the calculated number of breaths per minute to the first respiration rate threshold fetched from the memory. If the number of breaths per minute is less than the first respiration rate threshold, the microcontroller 110 identifies an apnea condition of the breathing and actuates the alarm 106 in the seizure alert mode. In an example, the first respiration rate threshold is 12 breaths per minute. If the number of breaths per minute are greater than the first respiration rate threshold, the microcontroller 110 compares the number of breaths per minute to the second respiration rate threshold. In an example, the second respiration rate threshold is 20 breaths per minute. When the number of breaths per minute are greater than the second respiration rate threshold, the microcontroller 110 identifies a tachyapnea condition of the breathing and actuates the alarm in the seizure alert mode. The microcontroller 110 is configured to identify normal breathing when the number of breaths per minute is between 12 breaths per minute and 20 breaths per minute. The first threshold and the second threshold may be set based on observation of the patient over a given time period. For example, a child may normally take 18 to 60 breaths per minute, where a geriatric patient may normally take no more than 10 breaths per minute and a patient with respiratory illness or heart disease may take 16 to 25 breaths per minute.

The microcontroller 110 is configured to identify an ictal stage of epileptic seizure by monitoring the high frequency phasic signals and the breaths per minute. The ictal stage is identified when the high frequency phasic signals are greater than the second skin conductance threshold value and the breaths per minute are greater than 12 breaths per minute.

The microcontroller 110 is configured to identify a postictal stage of an epileptic seizure by monitoring the high frequency phasic signals and the breaths per minute. The postictal stage is identified when the high frequency phasic signals are less than the first skin conductance threshold value and the breaths per minute are less than 20 breaths per minute.

The display screen 112 is mounted on an exterior surface of the wearable chest band 116. The display screen 112 is commutatively coupled to the microcontroller 110. Based on the comparison of the high frequency phasic signals and the respiratory rate signals, the microcontroller 110 is further configured to display any one of "Preictal Stage", "Ictal Stage", "Post Ictal Stage", "Apnea", "Normal Breathing", "Tachyapnea", "Warning" and "Seizure" on the display screen 112.

The microcontroller 110 is further configured to generate a communications packet. In an example, the communications packet includes the low frequency tonic signals, the high frequency phasic signals, the number of breaths per minute, the warning alert and the seizure alert. The micro-controller 110 is operatively connected to the communica-tions device 114. In an example, the communications device 114 includes an RF interface. The communications device 114 is configured to transmit the communications packet to the smart device 140. The device 100 and the user device may have communications capabilities that include, but are not limited to, GPS, Bluetooth Low Energy (BLE), ESP32 (an integrated WiFi and dual mode Bluetooth unit), Wi-Fi, EDGE, 2G, 3G, 4G, LTE, wired network, Bluetooth®, Near Field Communications (NFC), Infrared (IR), etc.).

For example, and without limitation, the smart device may refer to a mobile device, Personal Digital Assistant (PDA), desktop computer, wearable object, smartwatch, wearable sensor, a cellular telephone, a tablet, a wearable watch, a fitness band, a netbook, a wireless terminal, a laptop computer, a wearable computer device, customized health monitoring device or any other device.

The device 100 is configured to communicate with the smart device 140 using any of a wired connection, or a wireless connection (e.g., Bluetooth® networks, WLAN networks, WiFi, etc.), a radiofrequency (RF) connection, an infrared connection, such as wireless broadband, ZigBee, Z-wave, ultra-wideband ("UWB"), infrared data association ("IrDA") communications, and the like.

The smart device 140 is configured receive the commu-nications packet from the device 100 by employing an epi-seizure telemedicine application 142. In some examples, the application may be a software or a mobile application from an application distribution platform. Examples of application distribution platforms include the App Store for iOS provided by Apple, Inc., Play Store for Android OS provided by Google Inc., and such application distribution platforms. The epi-seizure telemedicine application 142 is configured to extract the information from the received communications packet. The epi-seizure telemedicine appli-cation 142 is configured to display the extracted information on a touchscreen of the smart device 140. For example, the extracted information is the warning alert, the seizure alert, and a prompt to press a stop command on the touchscreen of the smart device 140.

In an operative aspect, after wearing the wearable chest band 116, the patient is required to connect the device 100, may be attached to the wearable chest belt, with the epi-seizure telemedicine application 142 in the smart device 140, such that the device 100 is configured for real-time transfer of the communications packet and is able to display the information on the epi-seizure telemedicine application 142. In one aspect, the smart device 140 and the device 100 may be connected automatically after analyzing the network and finding a previously connected device.

FIG. 1B is an exemplary overview 150 of the device 100. Each patient has different health indicators. Therefore, it is preferable to examine health indicators of the patient and identify the examined health indicators as baseline levels or values of the patient in a relaxed state. As shown in FIG. 1B, an object of the device 100 is to monitor the health indicators (health desirable parameters). The device 100 is considered the health desirable parameters in a normal condition as a baseline for each patient and all the operations are based upon the considered baseline (acts as a threshold value). The device 100 has an initialization phase. Each time during the initialization phase, when the patient wears the device, the device 100 is configured to measure health indicators of the patient and set them as the threshold values, thereby providing an accurate and robust device. In an example, the device 100 monitors the following health desirable param-eters:

1. If the EDA of the patient exceeds the threshold value, an alarm will be sent to the caregiver, which is con-sidered the prediction phase.
2. If both the EDA and respirate rate (RR) exceed the threshold's condition, an alarm will be sent to the caregiver, which is considered the detection phase.

After receiving the alarm during both phases, the care-giver is supposed to check on the patient's condition. After checking the patient, the caregiver has an option for pressing a stop button located on the wearable chest band. In an example, the stop button may be located on the epi-seizure telemedicine application 142 as the prompt.

EDA is determined by applying a constant voltage (known as skin conductance (SC) in DC measurements) through the skin, and the current flowing through the skin is recorded. Using the above mentioned approach, the device is configured to determine the tonic component and the phasic component. The tonic component and the phasic component are added together to generate the EDA signal in microSiemens (µS).

Phasic components are defined as transient variations in the skin conductance caused by a stimulus. For example, the phasic components occur within 1-3 seconds after the stimu-lus starts. In relaxed state, phasic amplitudes normally vary between a threshold 0.01 µS to 3 µS, with a rise time between 0.5-3.5 seconds. The phasic components indicate the response features of EDA and may be collected, evalu-ated, and categorized for the purpose of seizure prediction and detection.

The tonic component is related to the slower components of the signal including the baseline of signal which also known as Skin Conductance Level (SCL). The tonic com-ponent (tonic level) refers as a background feature of a signal and slows acting components, such as overall tonic level, gradual ascents, and declinations over time. For example, the tonic component of an individual changes throughout time, based on his/her psychological condition. In an example, an average value of the tonic component may vary between 2 µS and 50 µS. The tonic component is not immediately linked to stimuli but rather reflects a more generalized state of arousal.

In the present disclosure, during experimentations, fol-lowing steps were employed in order to separate the EDA signal into the tonic component and the phasic component respectively:

1. Sampling:
The standard frequency range of the EDA frequency signal ($f_{max}$) is 0-2 Hz, and the sampling frequency ($f_s$) must be greater than or equal to two times the original frequency signal as provided below in Equation (1).

$$f_s \geq 2f_{max} \tag{1}$$

2. Filtering
The tonic component has a frequency bandwidth of 0-0.05 Hz, whereas the phasic component has a frequency bandwidth of 0.05-2 Hz. A second order LPF (for example, a second order Butterworth LPF) with a cut off frequency of 0.05 Hz was used to extract the tonic component from the raw electrical signal (received from the electrodes). The second order Butterworth LPF had a passband frequency response as flat as possible.

3. Phasic Extraction

The phasic component was found by subtracting the obtained tonic component from the raw electrical signal. For example, the threshold value of the phasic component was set between 15-20 μS, which range is an indication that the prediction phase has begun (preictal phase). Subsequently, when the signal reached 20 μS or greater, the detection phase started (from ictal phase until postictal phase).

Figure 1C:
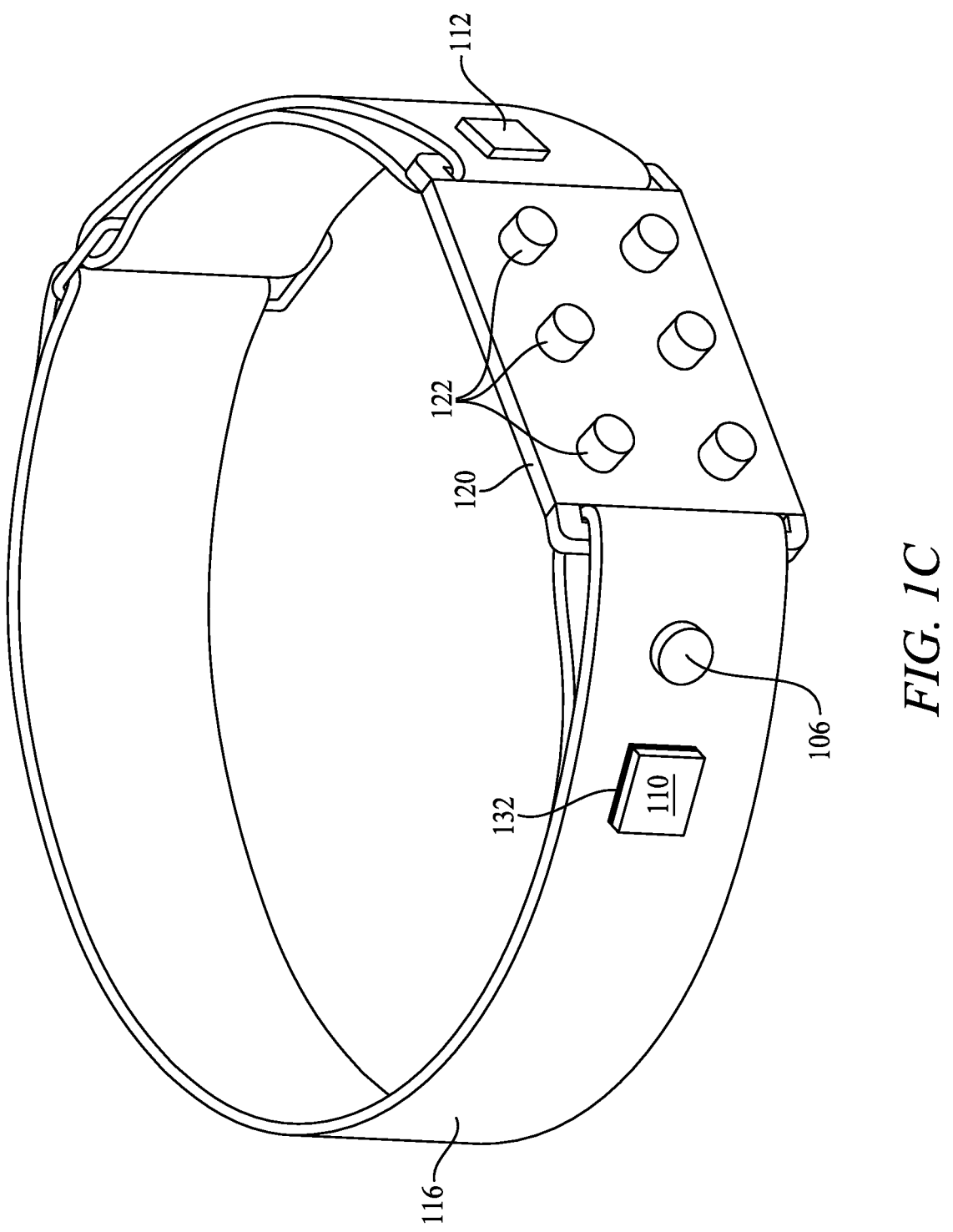
FIG. 1C is an exemplary overview of an inner surface of a rigid outer band secured on a wearable chest band, according to certain embodiments.
Figure 1D:
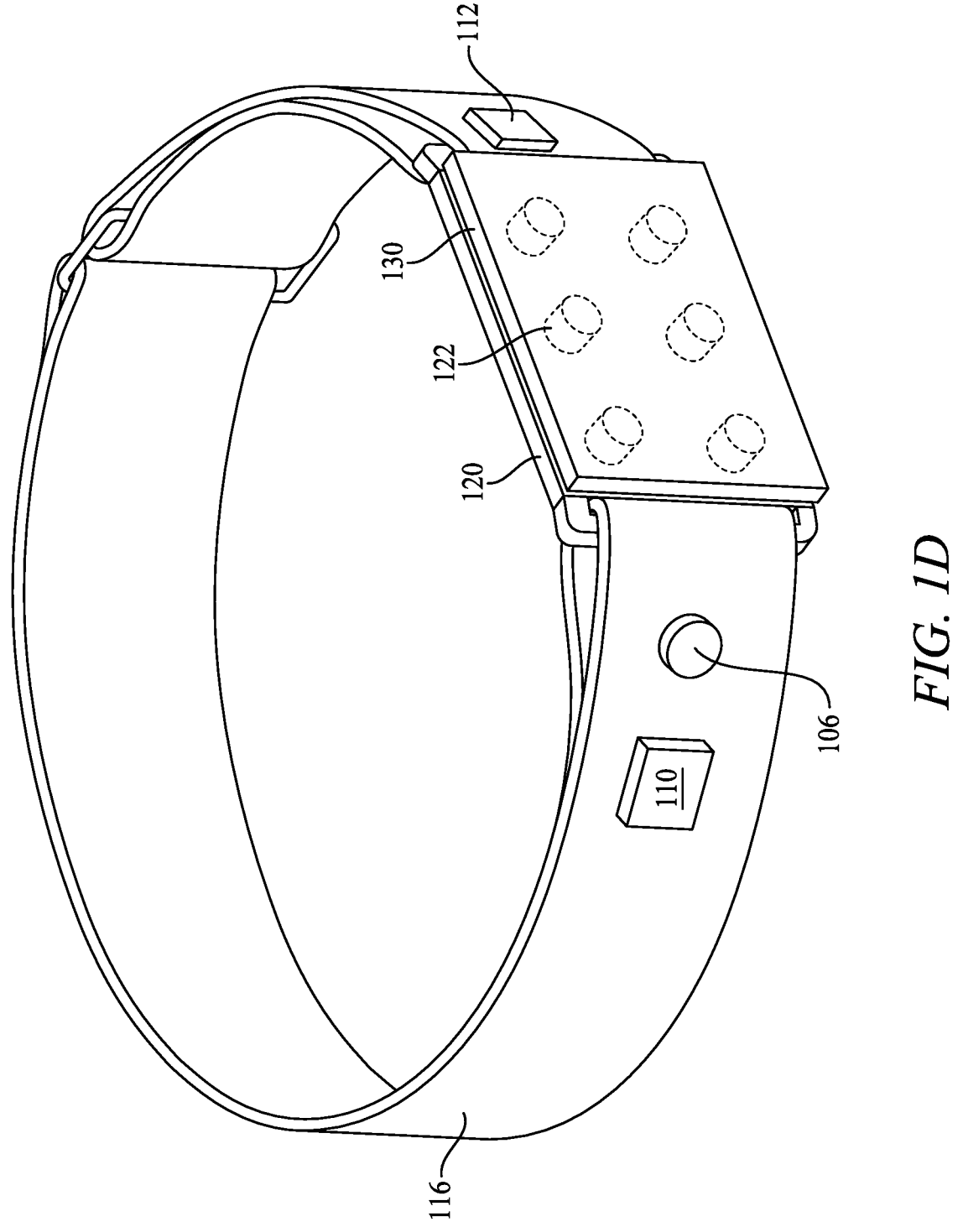
FIG. 1D is an exemplary overview of the wearable chest band, according to certain embodiments.

FIG. 1C is an exemplary overview of an exterior surface of the wearable chest band 116, according to certain embodiments. As shown in FIG. 1C, the alarm 106, the microcontroller 110, the display screen 112 are attached with the wearable chest band 116. Further, the device 100 includes the rigid rectangular plate 120, a plurality of motion sensors 122, the rigid outer band (as shown in FIG. 1D), and an attachment 132. FIG. 1C illustrates the exterior surface of the wearable chest band 116 when the rigid outer band is not placed over the rigid rectangular plate 120. The rigid rectangular plate 120 is mounted to the exterior surface of the wearable chest band 116. The plurality of motion sensors 122 is mounted around a perimeter of the rigid rectangular plate 120.

The wearable chest band (respiratory sensor belt) 116 is adapted to be flexibly wrapped around the chest of the patient. Specifically, the wearable chest band 116 is placed around the intercostal muscles which act as the active locations for detecting the chest movements. To provide a comfortable wearing experience to the patient, the wearable chest band 116 may be made of flexible materials such as, but not limited to, viscoelastic material, braided cotton and latex. In some aspects, an inner surface of the wearable chest band 116 that contacts the chest of the patient may be provided with an anti-sweat lining. The viscoelastic material may include, but is not limited to, thermoset elastomers (rubber), thermoplastic elastomers (TPE), thermoplastic vulcanizates, silicones, and/or polyurethanes (including thermoplastic polyurethanes (TPU)).

The attachment 132 is configured to hold the microcontroller 110 on the wearable chest band 116 next to the rigid rectangular plate 120. In an example, the attachment 132 includes a Velcro strap, a hook and loop or other mechanical mating surfaces that attaches to the exterior surface of the wearable chest band.

As shown in FIG. 1C, the plurality of pneumatic plungers 124 is located perpendicularly to the wearable chest band 116. The pneumatic plungers 124 are enclosed within the rigid outer band 130 and the rigid rectangular plate 120. As the chest expands when the patient inhales, the pneumatic plungers 124 are compressed between the rigid outer band 130 and the rigid rectangular plate 120. When the chest relaxes when the patient exhales, the pneumatic plungers 124 extend. In an example, the rigid rectangular plate 120 holds a magnet, and the rigid outer band 130 holds a diametrically placed hall sensor (electric field sensor, magnetic field sensor) at the positions where the pneumatic plunger 124 connects to the rigid outer band 130. The Hall sensor detects the presence and magnitude of the magnetic field using the Hall effect. The Hall sensor converts the change in the magnetic field into electric signals (respiratory rate signals). Abrupt changes in the intensity of the magnetic field are indicative of the inhalations and exhalations of the patient.

FIG. 1D is an exemplary overview of the exterior surface of the wearable chest band 116 having the rigid outer band 130, according to certain embodiments. As shown in FIG. 1D, the rigid outer band 130 is configured to attach over the rigid rectangular plate 120. FIG. 1D shows a front view of the rigid outer band 130. The rigid outer band 130 is connected to the wearable chest band 116 so as to compress each motion sensor 122 against the rigid rectangular plate 120 as the chest rises. The motion sensors 122 are configured to generate respiratory rate signals.

Figure 1F:
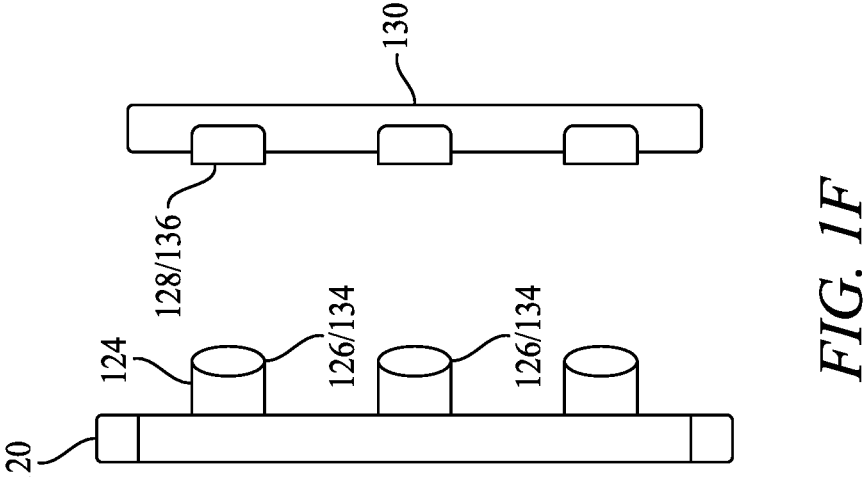
FIG. 1F is an exemplary view between a rigid rectangular plate and the rigid outer band, according to certain embodiments.
Figure 1E:
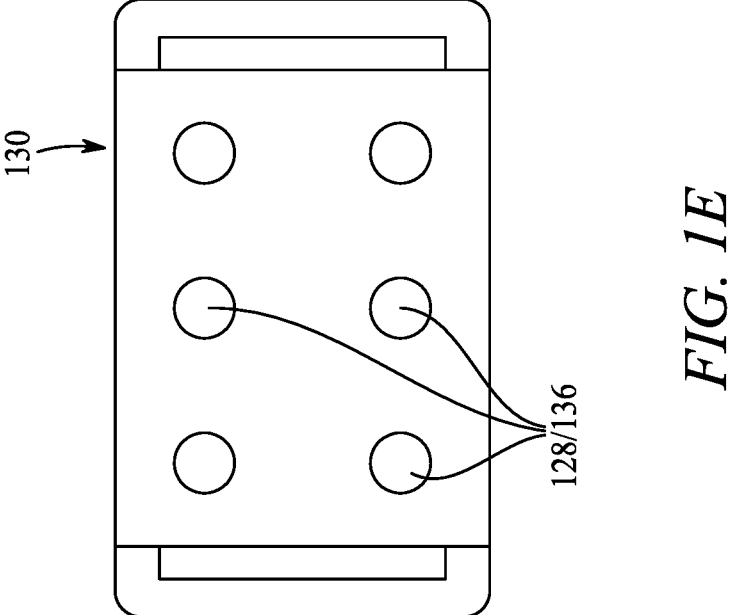
FIG. 1E is an exemplary inner view of the rigid outer band, according to certain embodiments.

FIG. 1E is an exemplary interior view (back view) of the rigid outer band 130, according to certain embodiments. As shown in FIG. 1E, a plurality of magnetic field sensors 128 is attached to the rigid outer band 130. Each magnetic field sensor 128 is configured to sense a magnetic field generated by a respective magnet and generate the respiratory rate signals in response to sensing the magnetic field. In an example, a plurality of electric field sensors is attached to the rigid outer band 130. Each electric field sensor is configured to detect a nearby object such as the conductive plate. In some examples, a plurality of capacitive sensors 136 is attached to the rigid outer band 130. The capacitive sensor detects a solid target or liquid target without physical contact. To detect the target, the capacitive sensors emit an electrical field from a sensing end of the sensor. The target that can disrupt the emitted electrical field can be detected by the capacitive sensor.

FIG. 1F is an exemplary view between the rigid rectangular plate 120 and the rigid outer band 130, according to certain embodiments. Referring to FIG. 1D-FIG. 1G, the motion sensors 122 include a plurality of pneumatic plungers 124. Each of the plurality of pneumatic plungers 124 rises and falls as a breath is inhaled and exhaled, respectively. In an example, the motion sensors 122 are selected from any one of linear motion sensors, piezoelectric sensors, strain sensors, hall sensors, capacitive sensors, pneumatic sensors and magnetic sensors.

Figure 1G:
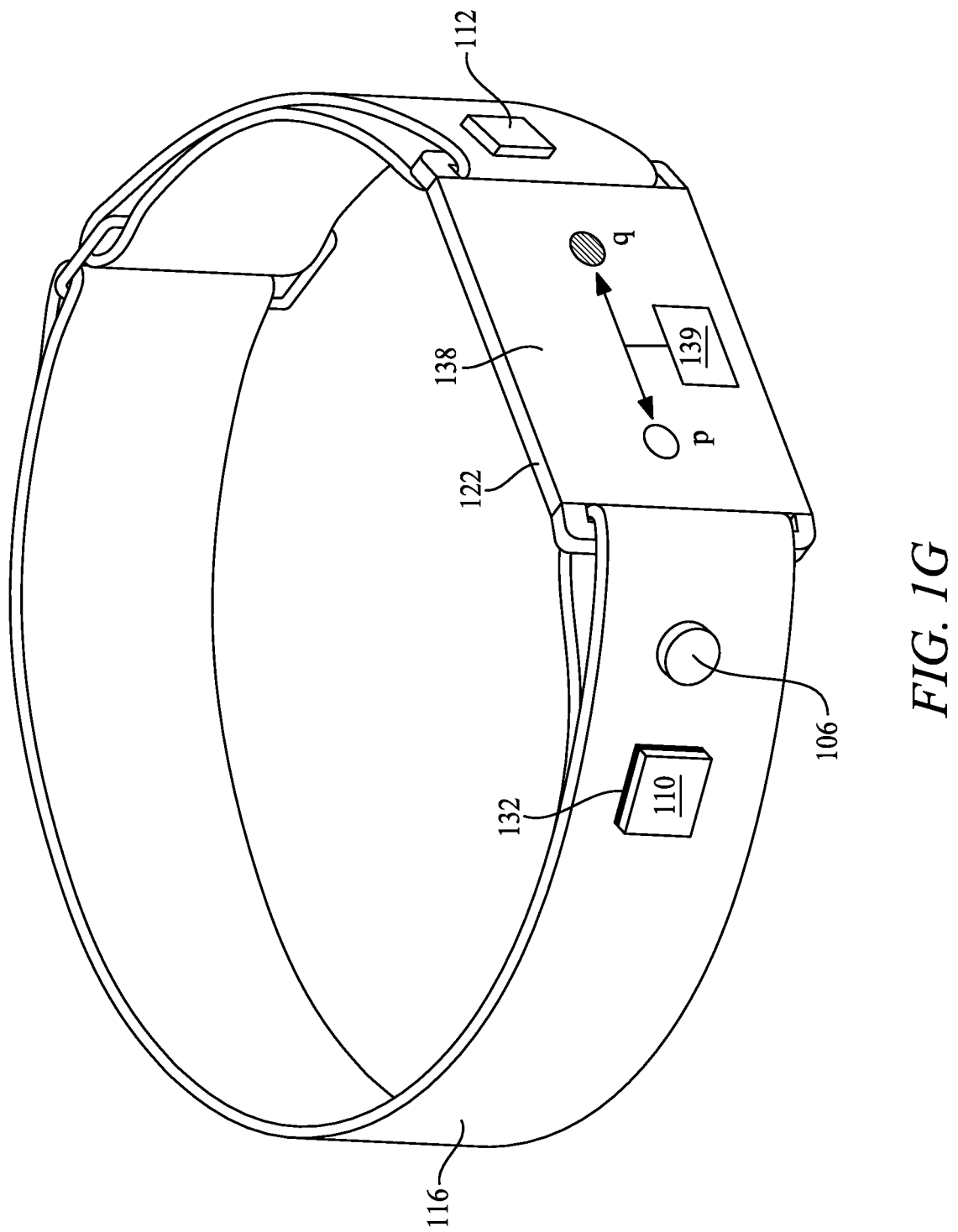
FIG. 1G illustrates an exemplary embodiment of a motion sensor having a stretchable band, according to certain embodiments.

FIG. 1G illustrates an exemplary implementation of the motion sensor 122 having a stretchable band 138. In this implementation, in order to measure the variations during inhalation and exhalation, a linearly sliding potentiometer may be used that measures the chest expansion as the patient breathes. The motion sensor 122 as shown in the figure is implemented in the stretchable band 138 having at least one conductive wire located/fabricated within the stretchable band 138. A linearly sliding potentiometer (voltage divider) 139 is located within the stretchable band 138. In an exemplary implementation, the linearly sliding potentiometer 139 is placed in the stretchable band 138. The linearly sliding potentiometer 139 is configured to measure the relative amount of expansion during respiration. The stretchable band 138 is configured to stretch and contract as a breath is inhaled and exhaled, respectively. As the length of the conductive wire varies according to the inhalation and exhalation of the user, a resistance associated with the conductive wire also varies simultaneously. The linearly sliding potentiometer 139 is configured to sense changes in resistance due to a change in the length of the conductive wire. In an example, the conductive wire has a fixed point (q) and a varying point (p). The motion sensor 122 is configured to generate the respiratory rate signals in response to the changes in the length of the conductive wire sensed by the linearly sliding potentiometer 139. The potentiometer 139 is configured to translate changes in resistance into changes in voltage (respiratory rate signals). The microcontroller 110 is coupled to the motion sensor 122 (the potentiometer 139) and is able to read a change in voltage.

In the present disclosure, the motion sensor 122 may be configured as any of three different structural configurations. In one configuration, each motion sensor 122 includes a pneumatic plunger 124, a magnet 126, and a plurality of magnetic field sensors 128. Each pneumatic plunger 124 is configured to rise and fall as a breath is inhaled and exhaled, respectively. The magnet 126 is attached to each pneumatic plunger 124. Each magnetic field sensor 128 is configured to sense a magnetic field generated by a respective magnet 126 and generate the respiratory rate signals in response to sensing the magnetic field.

In another configuration, each motion sensor 122 includes a pneumatic plunger 124, a conductive plate 134, and a plurality of capacitive sensors 136. The conductive plate 134 is attached to each pneumatic plunger 124. The conductive plate 134 is attached to each pneumatic plunger 124. The plurality of capacitive sensors 136 is attached to the rigid outer band 130. Each capacitive sensor 136 is configured to sense changes in an electric field due to the proximity of each conductive plate 134 as the respective pneumatic plunger 124 rises and falls and generates respiratory rate signals in response to the changes in the electric field.

In a third configuration, the motion sensor 122 includes a linearly sliding potentiometer configured to measure change in resistance in the wearable chest band 116 due to expansion and depletion of the chest as shown in FIG. 1G.

In an example, the device 100 is configured to predict motor seizures and non-motor seizures (absence seizures). For example, the non-motor seizures may have following symptoms:

1. staring into space;
    2. a sudden stop in movement;
    3. brief twitches; and
    4. fluttering eyelids.

Figure 2:
FIG. 2 is a block diagram of a system for predicting and monitoring epileptic seizures, according to certain embodiments.

FIG. 2 is an overview of a system 200 for predicting and monitoring epileptic seizures, according to certain embodiments. As shown in FIG. 2, the system 200 includes a wearable EDA sensor 202, a wearable RR sensor 204, an alarm 206, a second order low pass filter 208, a microcontroller 210, a display screen 212, a communications device 214, and a smart device 240.

The construction and operation of the system 200 are substantially similar to the device 100, as disclosed in FIG. 1A-FIG. 1E, and thus the construction and operation are not repeated here in detail for the sake of brevity.

The wearable EDA sensor 202 is configured to measure skin conductance and generate EDA signals. The EDA sensor 202 is configured to detect changes in the electrical properties of the skin in response to stress or anxiety or before an epileptic seizure. The EDA sensor 102 measures the electrical properties of the skin by recording the electrical resistance of the skin by passing a low voltage current or by recording weak currents generated by the body during stress or anxiety. For example, the system 200 includes the hand wrap that is configured to secure the EDA sensor 202 around the set of fingers of the patient. The hand wrap includes two nickel electrodes located so as to contact a medial phalange of each of an index finger and a middle finger.

The wearable RR sensor 204 is configured to measure the chest movement of the patient and generate respiratory rate signals. The wearable RR sensor 204 includes a plurality of motion sensors. In a first structural configuration, each of the plurality of motion sensors includes a pneumatic plunger, a conductive plate, and a capacitive sensor. In another configuration, the motion sensor includes the pneumatic plunger, a magnetic plate, and a magnetic sensor. In each construction, the pneumatic plunger is configured to rise and fall as a breath is inhaled and exhaled, respectively. In the first structural configuration, the conductive plate is attached to the pneumatic plunger. As each pneumatic plunger rises and falls, its capacitive sensor is configured to sense changes in an electric field due to a change in the proximity of the conductive plate from the electric field sensor. Each motion sensor is configured to generate the respiratory rate signals in response to the changes in the electric field sensed by the capacitive sensor. In the second structural configuration, a magnet is attached to the end of the pneumatic plunger. The pneumatic plunger is configured to rise and fall as a breath is inhaled and exhaled, respectively, towards and away from a magnetic field sensor. Each motion sensor is configured to generate the respiratory rate signals in response to the changes in the magnetic field sensed by the magnetic sensor. The wearable RR sensor 204 is located in or on the wearable chest band. The microcontroller 210 receives the electrical signals generated by the capacitive sensor or the magnetic sensor and converts the signals to breaths per minute.

The second order LPF 208 is operatively connected to the EDA sensor 202 and receives the EDA signals from the EDA sensor 202. In an example, the second order LPF 208 has a cut-off frequency of 0.05 Hz. The second order LPF 208 is configured to filter the EDA signals by removing low frequency tonic signals and generating high frequency phasic signals having frequencies greater than 0.05 Hz. In an example, the low frequency tonic signals have frequencies less than 0.05 Hz.

The alarm 206 is configured to generate an alarm signal. The alarm 206 is configured to operate in a warning mode and a seizure alert mode. In an example, the alarm 206 is a visual alarm and an audio alarm. The visual alarm includes a plurality of LED lights. For example, a green LED may indicate the warning mode, and a red LED may indicate the seizure alert mode. In an example, the audio alarm includes a speaker. The audio alarm is configured to generate a voice message. For example, in the warning mode, the speaker may play a voice message "be careful, a seizure is expected". In the seizure alert mode, the speaker may play a voice message "seizure, please help", "call emergency", or the like.

The microcontroller 210 is connected to the communications device 214, the EDA sensor 202 and the RR sensor 204. The microcontroller 210 is configured to receive the high frequency phasic signals and compare an amplitude of the high frequency phasic signals to a first skin conductance threshold value and a second skin conductance threshold value.

When the amplitude of the high frequency phasic signals is greater than the first skin conductance threshold value but less than the second skin conductance threshold value, the microcontroller 210 actuates the alarm in the warning mode.

When the amplitude of the high frequency phasic signals is greater than or equal to the second skin conductance threshold value, the microcontroller 210 receives the respiratory rate signals and calculates a number of breaths per minute based on the respiratory rate signals. The microcontroller 210 compares the number of breaths per minute to a first respiration rate threshold. When the number of breaths per minute is less than the first respiration rate threshold, the microcontroller 210 is configured to identify an apnea condition of the breathing and actuate the alarm in the seizure alert mode.

When the number of breaths per minute is greater than the first respiration rate threshold, the microcontroller 210 is configured to compare the number of breaths per minute to a second respiration rate threshold.

If the number of breaths per minute is greater than the second respiration rate threshold, the microcontroller 210 is configured to identify a tachyapnea condition of the breathing and actuate the alarm in the seizure alert mode.

The microcontroller 210 is configured to generate a communications packet including the low frequency tonic signals, the high frequency phasic signals, the number of breaths per minute, the warning alert and the seizure alert, and transmit the packet to the smart device 240 which is configured with the epi-seizure telemedicine application 242. The epi-seizure application is configured to display the any one of the warning alert, the seizure alert, and a prompt to press a stop command on a touchscreen of the smart device 240.

The microcontroller 210 is further configured to generate a communications packet. In an example, the communications packet includes the low frequency tonic signals, the high frequency phasic signals, the number of breaths per minute, the warning alert, and the seizure alert. The communications device 214 is operatively connected to the microcontroller 210. The communications device 214 is configured to transmit the communications packet to the smart device 240.

The communications device 214 is configured to transmit the communications packet by using a near field transceiver 216.

The smart device 240 includes an epi-seizure telemedicine application 242, a near field receiver 244, and a registration database 246. The smart device 240 is configured to receive the communications packet with the near field receiver 244.

The smart device 240 is configured to receive the communications packet from the microcontroller 210, using the communications device 214, by downloading the epi-seizure telemedicine application 242 over a data communication network from a cloud server 248. In an aspect, the epi-seizure telemedicine application 242 is stored in the cloud server 248. The smart device 240 is registered with the epi-seizure telemedicine application 242 and stores an instance of the epi-seizure telemedicine application 242. The microcontroller 210 is registered with the instance of the epi-seizure telemedicine application 242 stored on the smart device 240.

In some examples, the epi-seizure telemedicine application 242 may be a software or a mobile application from an application distribution platform. Examples of application distribution platforms include the App Store for iOS provided by Apple, Inc., Play Store for Android OS provided by Google Inc., and such application distribution platforms. The epi-seizure telemedicine application 242 is configured to extract the information from the received communications packet. The epi-seizure telemedicine application 242 is configured to display the extracted information on the smart device 240. For example, the extracted information is the warning alert, the seizure alert, and a prompt to press a stop command on a touchscreen of the smart device 240.

The registration database 246 is operatively connected with the epi-seizure telemedicine application 242. The epi-seizure telemedicine application 242 is configured to display a prompt on the touchscreen of the smart device 240 requesting registration of the microcontroller with the epi-seizure telemedicine application 242. The epi-seizure telemedicine application 242 is configured to prompt the patient or the caregiver to input registration data through the smart device 240, register the microcontroller 210 and store the registration data in the registration database 246.

In an operative aspect, after wearing the wearable chest band, the patient may connect the communications device 214 attached to the chest belt with the epi-seizure telemedicine application 242 in the smart device 240, such that the communications device 214 performs real-time transfer of data and is able to display the information on the epi-seizure telemedicine application 242.

The epi-seizure telemedicine application 242 is configured to deliver an epileptic seizure alert to an emergency contact(s), a doctor, a hospital, or any combination thereof.

Figure 3A:
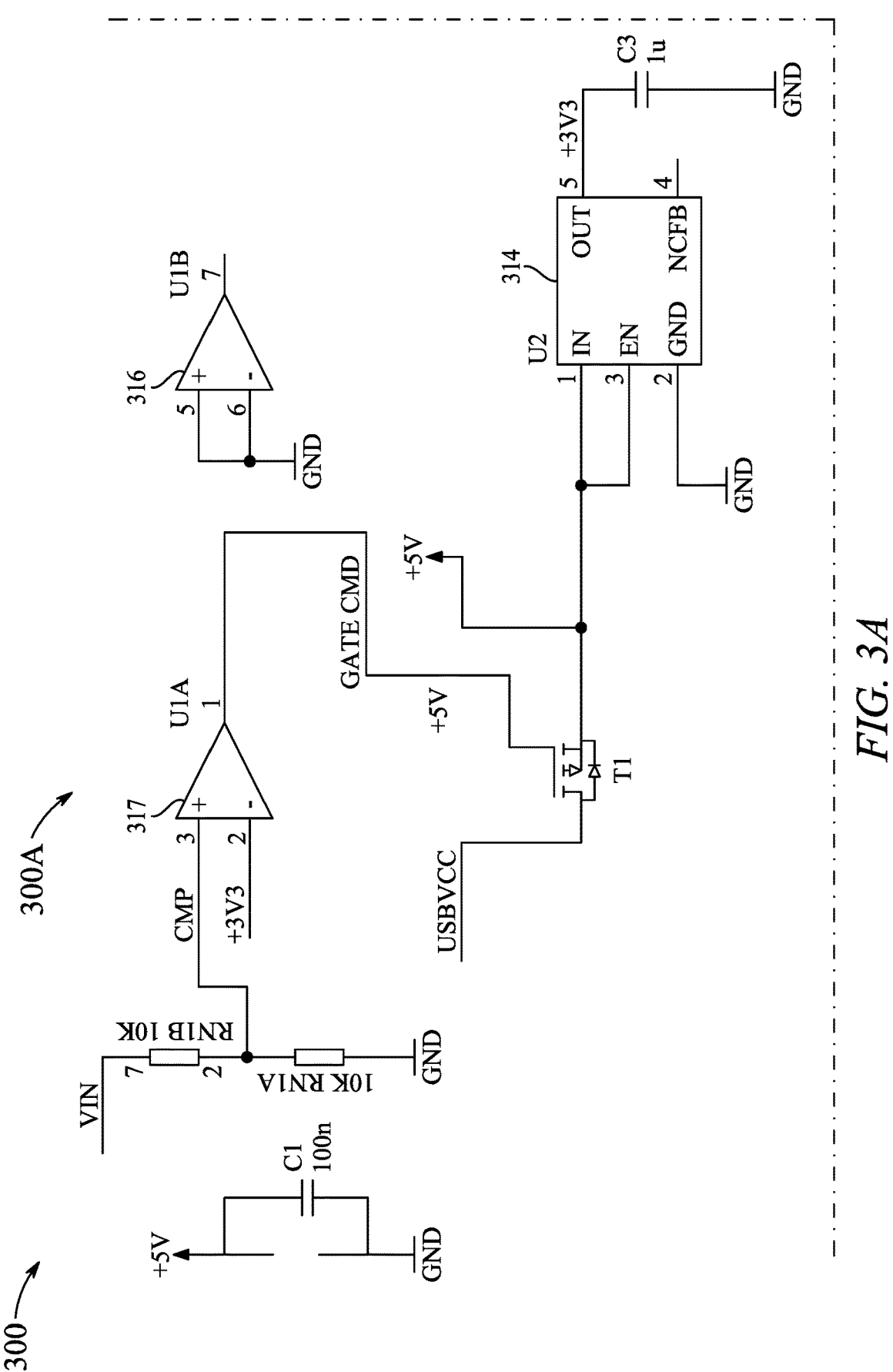
FIG. 3A is an electrical circuit diagram of a microcontroller, according to certain embodiments.
Figure 3A:
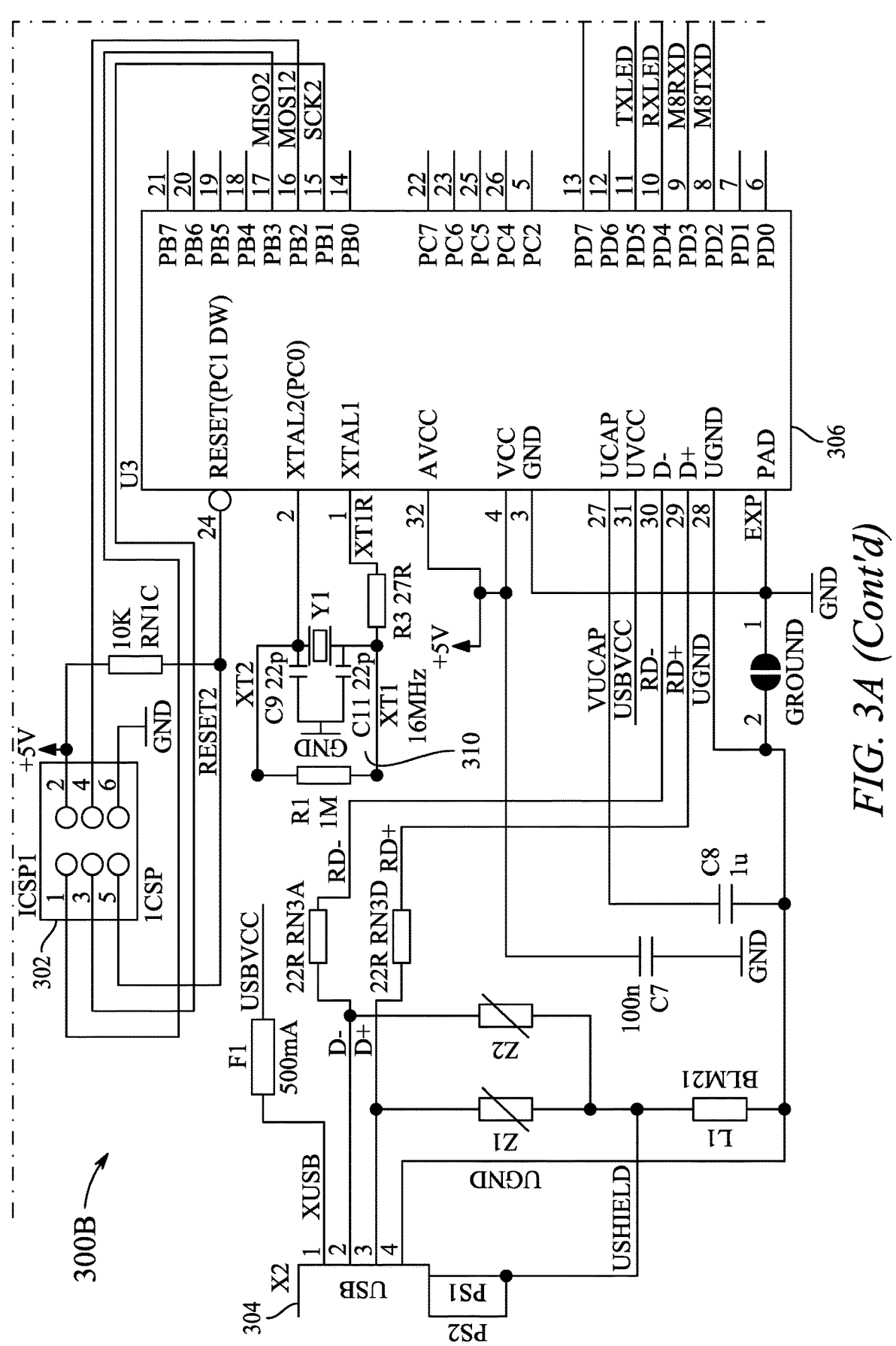
Figure 3A:
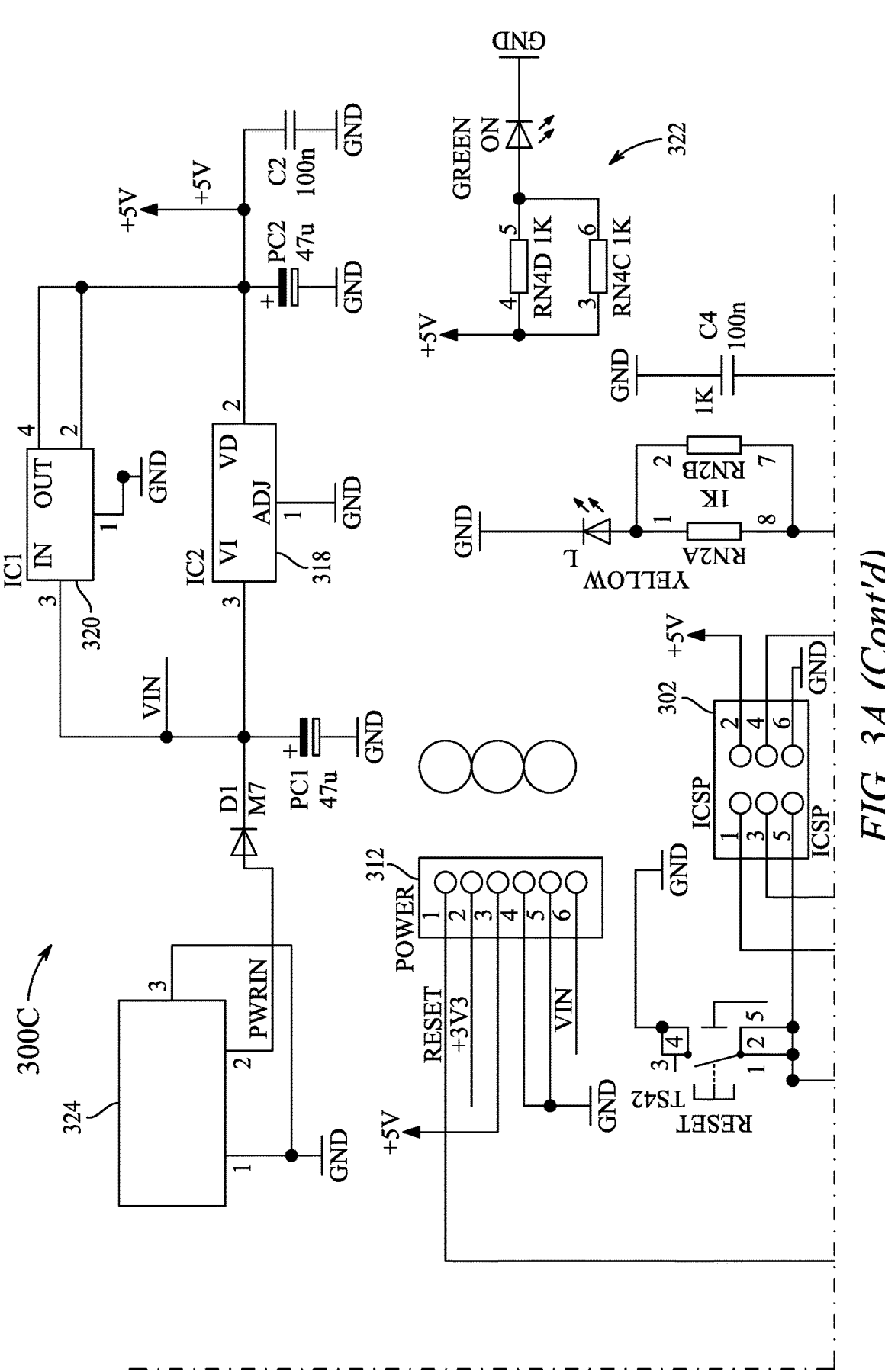
Figure 3A:
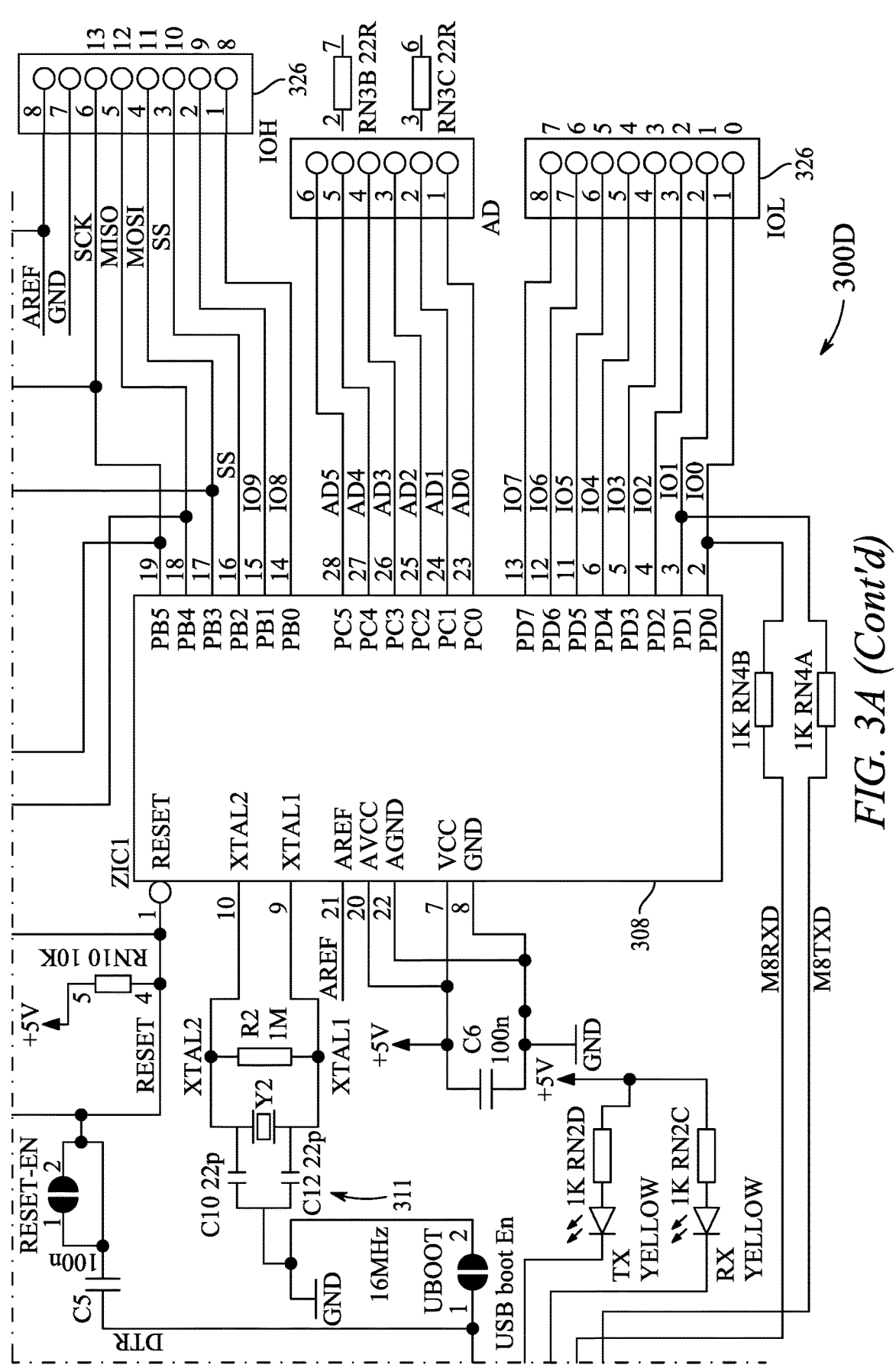

FIG. 3A is an electrical circuit 300 of the microcontroller 110 as connected to various electrical components, according to certain embodiments. In an example, the components of the disclosure may be connected and controlled via Arduino Uno (an open-source electronics platform that consists of a hardware and software). As shown in FIG. 3A, the electrical circuit 300 includes two programming chips 302, a Universal Serial Bus (USB) port 304, two microcontrollers 306, 308 (having a master slave configuration), two crystal oscillators 310, 311, where crystal oscillator 310 is connected to the 1 and 2 pins of 306 and crystal oscillator 311 is connected to the 9 and 10 pins of 308, two power sources (312, 324), a voltage regulator 314 connected to a comparator circuit formed by two operational amplifiers 316, 317 and switch T1, a linear voltage regulator 318, a three-terminal voltage regulator 320, a light-emitting diode (LED) 322, and two output terminals 326. In an aspect, the microcontroller 306 acts as a master microcontroller, and the microcontroller 308 acts as a slave microcontroller.

The basic construction and operative principles of all the electrical components shown in FIG. 3A is known in the art. These are commercially available products. Therefore, the construction and working of the electrical components are described here only briefly for the sake of understanding.

FIG. 3A has been shown across multiple sheets due to space constraints. A portion of FIG. 3A represented by 300A shows the voltage regulator 314 for regulating input supply USBVCC (USB 304 shown in 300B and the supply is connected to pin 31 of the microcontroller 306). A portion of FIG. 3A represented by 300B shows the programming chip 302, the USB 304, the microcontroller 306 (for example, configured as a master microcontroller) and the crystal oscillator 310 (providing clock signals to the microcontroller 306 at pin 1 and pin 2). Signals from the USB 304 are connected to the pin 27-pin 31 of the microcontroller 306. A portion of FIG. 3A represented by 300C shows the second programming chip 302, the power source 312, the linear voltage regulator 318, the three-terminal voltage regulator 320, the LED 322 and the power source 324. The linear voltage regulator 318 and the three-terminal voltage regulator 320 regulate the power source 324 to provide supply to the microcontroller 308 at pin 7 and pin 20. The programming chip 302 is used to control the microcontroller 308 at pin 1. (providing clock signals to the microcontroller 306 at pin 1 and pin 2). A portion of FIG. 3A represented by 300D shows the crystal oscillator 311, the microcontroller 308 and the output terminals 326. The crystal oscillator 311 provides clock signals to the microcontroller 308 at pin 9 and pin 10. The microcontroller 308 provides output through pin 14-pin 19, and pin 23-pin 28. In a non-limiting example, the operational amplifiers 316, 317 are LM358D (manufactured by Texas Instruments, located at Dallas, Texas, United States of America). In another non-limiting example, the voltage regulator 314 is LP2985-33DBVR (manufactured by Texas Instruments, located at Dallas, Texas, United States of America). In a non-limiting example, the microcontroller 308 is ATMEGA8 (manufactured by Atmel Corp, located at 2325 Orchard Parkway, San Jose, California 95131, U.S.A.). In a non-limiting example, the microcontroller 306 is ATMEGA8U2-MU (manufactured by Microchip Technology Inc., located at 2355 West Chandler Blvd. Chandler, Arizona, U.S.A.).

Figure 3B:
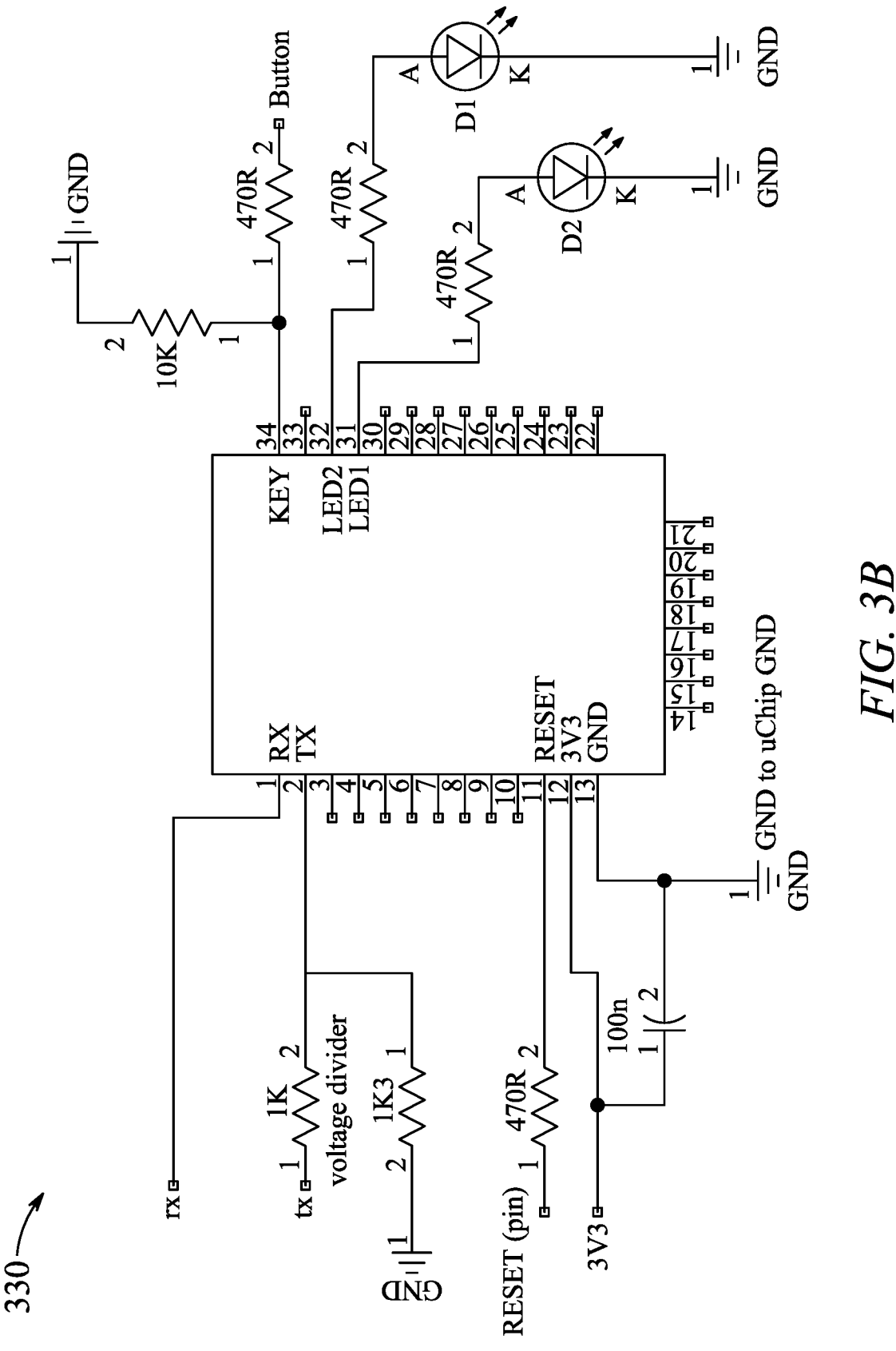
FIG. 3B is an electrical circuit diagram of a communications device, according to certain embodiments.

FIG. 3B is an electrical circuit diagram 330 of the communications device (for example Bluetooth), according to certain embodiments. The basic construction and operative principle of Bluetooth is known and therefore, the construction and working are only briefly described here for the sake of brevity. LED 1 at pin 31 is a blue LED configured to light when the communications device is ON. LED 1 is connected to pin 31 through a 470Ω resistor. LED 1 indicates the status of the communications device and may blink as follows: blink once in 2 sec: Module has entered Command Mode; repeated Blinking: waiting for connection in Data Mode; blink twice in 1 sec: connection successful in Data Mode. LED2 at pin 32 is a red LED D1 configured to light when the communications device is OFF. D2 is connected to LED1 at pin 31 through a 470Ω resistor. Each LED is connected to ground. TX at pin 34 is a transmitter and RX at pin 33 is a receiver. The pin 33 is connected to a voltage divider formed by the two 1 KΩ resistors. A RESET button is connected to pin 11 through a resistance of 470Ω. A voltage source 3V3 is connected to pin 12. A 100 nF capacitor is connected between the voltage source 3V3 and a ground, to ground the communications device at pin 13. Pin 34 is an ENABLE/KEY.

A button connected to this pin is used to toggle between a Data Mode (set low) and an AT command mode (set high). Data mode is the default mode. The button is connected to the KEY pin 34 through a voltage divider formed by a 470Ω resistor and a 10 KΩ resistor. (In an aspect, the device 100 can communicate with, for example, seven smart devices in a piconet (an ad-hoc computer network using Bluetooth technology). In an aspect, the communications device may be an HC-05 Bluetooth module, manufactured by James Electronics, Belmont, California, United States. The communications device shown in FIG. 3B is the HC-05 Bluetooth module, but the communications device of the present disclosure may be any one of GPS, Bluetooth Low Energy (BLE), ESP32 (an integrated WiFi and dual mode Bluetooth unit), Wi-Fi, EDGE, 2G, 3G, 4G, LTE, wired network, Bluetooth®, Near Field Communications (NFC), Infrared (IR), etc.). In an aspect, the communications device may be an ESP32-PICO-MINI-02, which is an integrated WiFi and dual mode Bluetooth unit, available from Espressif, Shanghai, China.

Figure 3C:
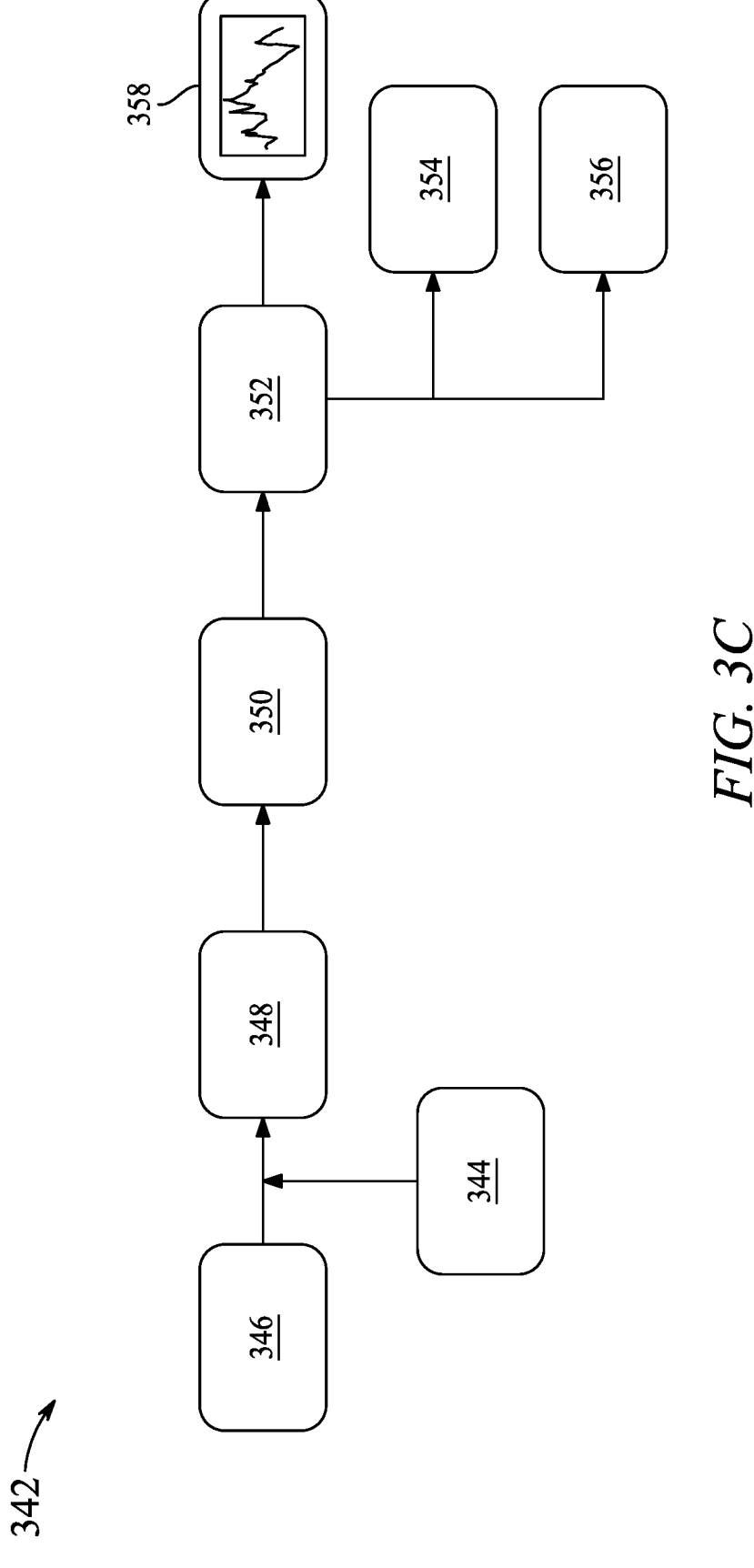
FIG. 3C is a schematic block diagram of an electrodermal activity (EDA) sensor, according to certain embodiments.

FIG. 3C is a schematic block diagram of the EDA sensor 342. A s shown in FIG. 3C, the EDA sensor 342 includes at least two nickel electrodes 344, a battery 346, a voltage divider 348, a Wheatstone bridge 350, a signal processing unit 352, a filter 354, an amplifier 356, and a display unit 358. In an example, the various components of the EDA sensor 342 such as the battery 346, the voltage divider 348, the Wheatstone bridge 350, the signal processing unit 352, the filter 354, and the amplifier 356 may be retained inside the hand wrap. The display unit 358 may be fitted on exterior of the hand wrap. The hand wrap secures the nickel electrodes 344 around the set of fingers of the patient.

The two nickel electrodes 344 come in contact with the medial phalange of each of the index finger and the middle finger. The two nickel electrodes 344 are configured to convert the chemical ion of the skin into the electric ion. The two nickel electrodes 344 are used due to their long-term stability and corrosion resistance.

The battery 346 is configured to supply power to the components of the EDA sensor 342 for proper functioning. In examples, the battery 346 is a battery may be a disposable dry cell battery, or a rechargeable battery that can be coupled to a charging device or connected or coupled to a standard outlet for electrical power.

The voltage divider 348 is configured to receive an input voltage ($V_{in}$) from the battery 346. The voltage divider 348 is configured to generate an output voltage ($V_{out}$) that is a fraction of the input voltage ($V_{in}$).

The Wheatstone bridge 350 is configured to detect the electric ion (weak signal) generated by the two nickel electrodes 344. The Wheatstone bridge 350 is configured to convert the weak signal into an electrical signal.

The signal processing unit 352 is configured to enhance various characteristics of the electrical signal and generates a processed output signal. The various characteristics include voltage, current, waveform distortion, power, etc.

The filter 354 is commutatively coupled to the signal processing unit 352 and receives the processed output signal from the signal processing unit 352. The signal processing unit 352 is configured to filter the processed output signal by removing the noise and generating a filtered signal.

The amplifier 356 is commutatively coupled to the filter 354 and receives the filtered signal. As the filtered signal is low, the amplifier 356 is employed to increase the power of the received signal. The amplifier 356 generates an amplified signal.

An optional display unit 358 is commutatively coupled to the amplifier 356. The display unit 358 is configured to display the received signal from the amplifier 356. In an example, the display unit 358 is as a LED matrix, small video display, high-resolution liquid crystal display (LCD), plasma, light-emitting diode (LED), or other devices suitable for displaying the amplified signal.

Figure 3D:
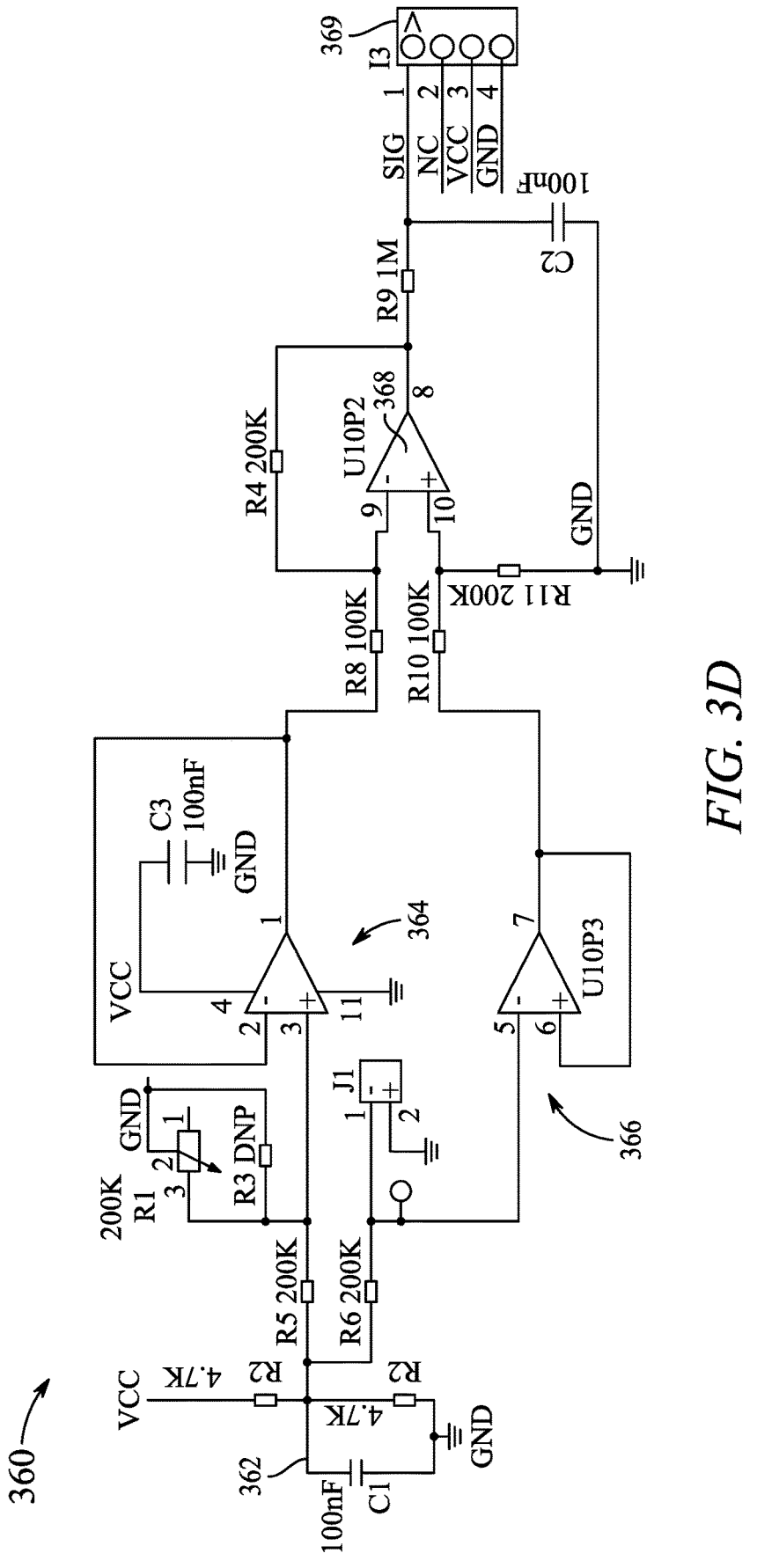
FIG. 3D illustrates an electrical circuit diagram of the EDA sensor, according to certain embodiments.

FIG. 3D illustrates an electrical circuit diagram 360 of the EDA sensor. As shown in FIG. 3D, the EDA sensor has a power source 362, three operational amplifiers (364, 366, 368), and an output terminal 369. In an example, the operational amplifier 364 is configured to receive electric ions at non-inverting input 3 generated by the first electrode and generate a first electrical signal. Operational amplifier 364 is configured to have unity gain. In a non-limiting example, the operational amplifiers (364, 366, 368) are amplifiers LM324PW (manufactured by Texas Instruments, located at Dallas, Texas, United States of America). The operational amplifier 366 is configured to receive electric ions at inverting input 5 generated by the second electrode and generate a second electrical signal. Operational amplifier 366 is also configured to have unity gain. The operational amplifier 368 has two input pins (9 and 10) and one output pin. Input pin 9 is connected to the output of operational amplifier 364. The operational amplifier 368 is configured to amplify and output the voltage difference between the two input pins. The output terminal 369 is configured to provide an output to another devices, such as the second order LPF or the microcontroller.

Figure 3E:
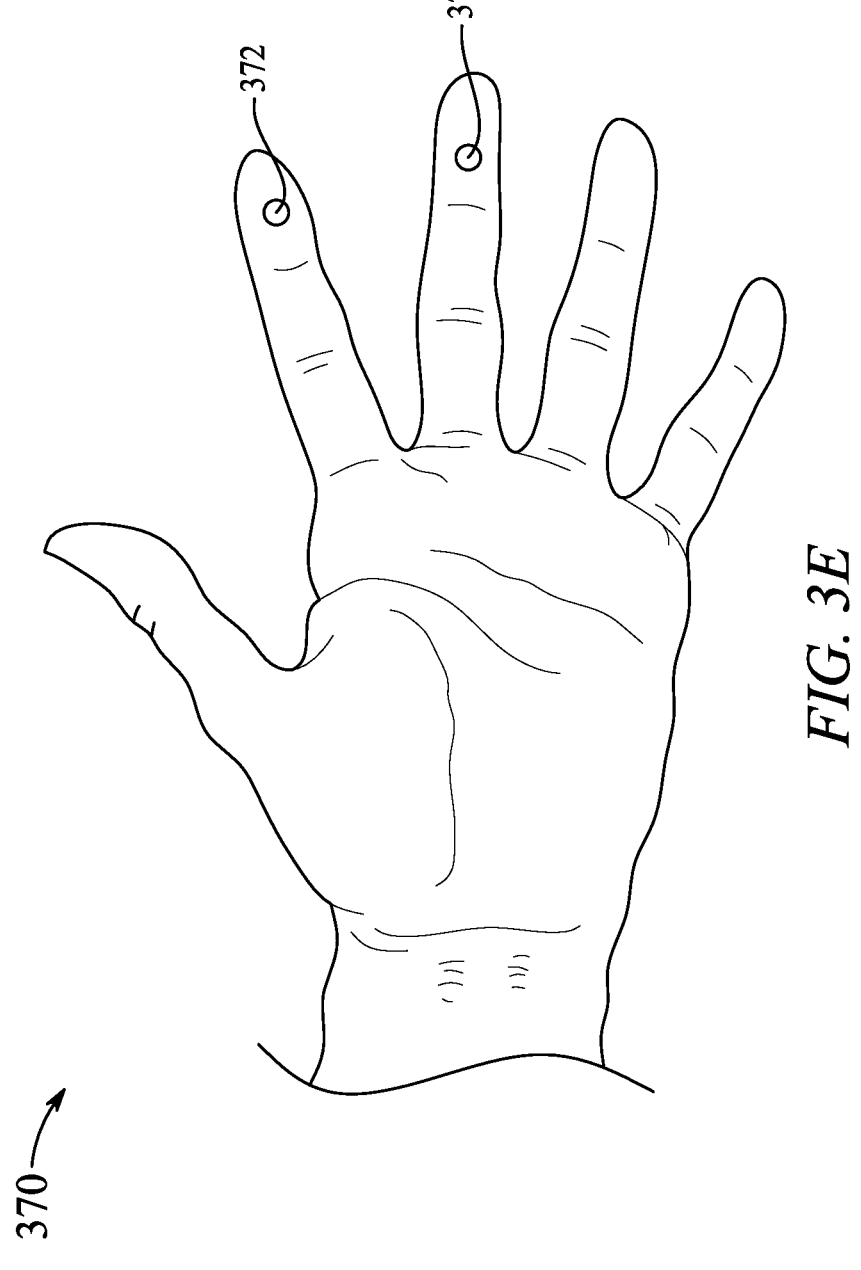
FIG. 3E is an exemplary placement of the EDA sensor on fingers of a patient, according to certain embodiments.

FIG. 3E is an exemplary placement 370 of the EDA sensor on fingers of the patient. The palmar surfaces of the hand are hairless and serve as active locations for EDA measurements. Palmar locations have high EDA due to the presence of a high number of eccrine sweat glands. For bipolar recordings, the medial phalanges of the index and middle fingers are preferred, as demonstrated in FIG. 3E. As shown in FIG. 3E, two nickel electrodes (372, 374) are fixed with the medial phalange of each of the index finger and the middle finger.

Figure 4A:
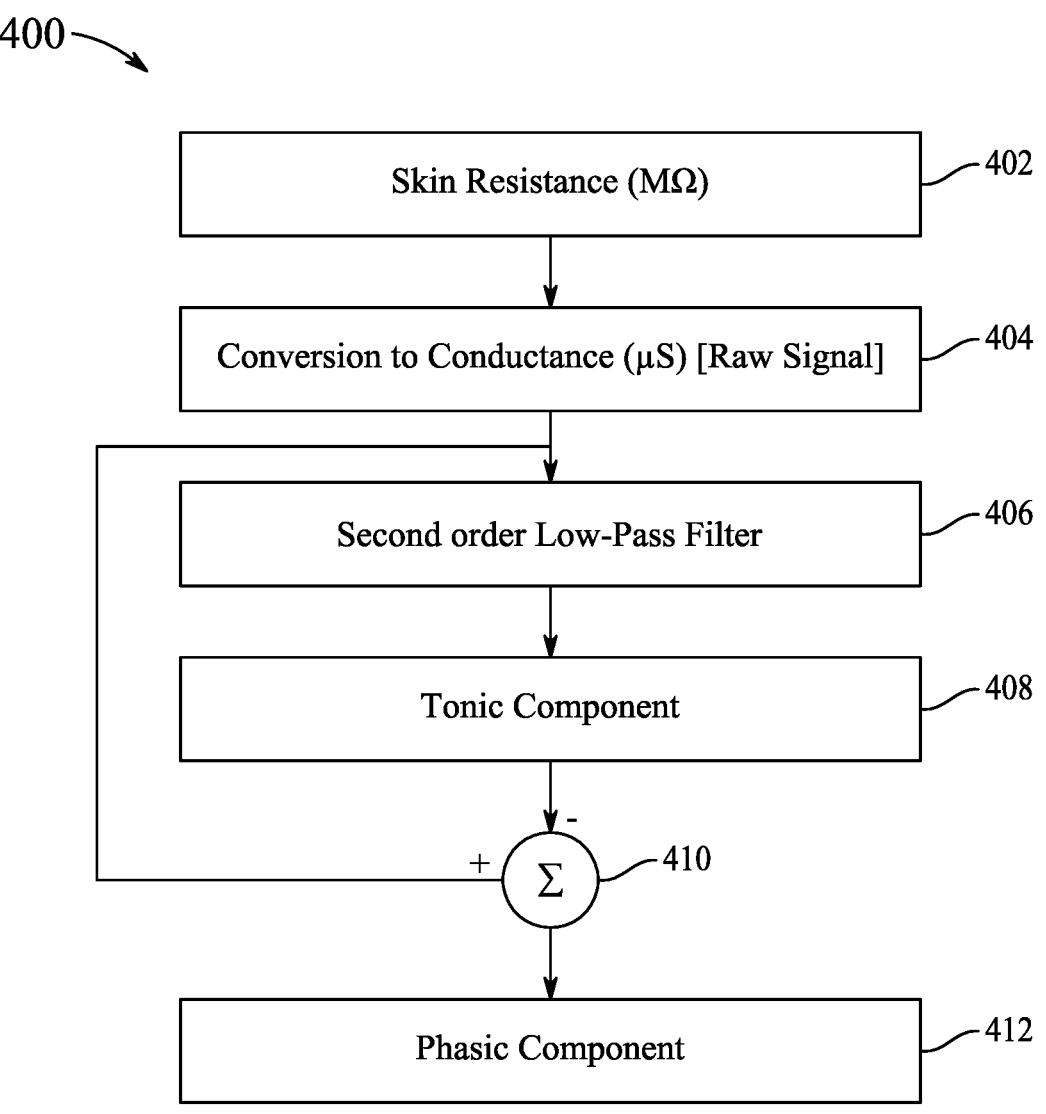
FIG. 4A is an exemplary flow chart of the EDA sensor, according to certain embodiments.

FIG. 4A is an electrodermal activity detection algorithm 400 performed by the EDA sensor 102. The EDA sensor 102 is wrapped around the hand of the patient. The EDA sensor 102 includes two nickel electrodes. The first nickel electrode contacts the medial phalange of the index finger, and the second one contacts the medial phalange of the middle finger.

Step 402 includes measuring the skin resistance using the EDA sensor 102. In an aspect, the EDA sensor 102 (a GSR (Galvanic Skin Reaction) sensor) is employed for measuring the electrical conductance of the skin. The electric conductance of the skin varies in proportion to moisture level of the skin. A value of the skin resistance varies based on mental or physiological arousal as per sweating produced by the skin. In an example, the EDA sensor 102 measures the electrical properties of the skin by recording the electrical resistance of the skin by passing a low voltage current or by recording weak currents generated by the body.

Step 404 includes converting the skin resistance to a skin conductance signal. The wearable EDA sensor 102 is configured to measure skin conductance of the patient directly and generating EDA signals (raw electrical signals).

Step 406 includes applying the EDA signal to the second order LPF 108. The second order low pass filter has the cut-off frequency of 0.05 Hz.

Step 408 includes filtering, by the second order LPF 108, the EDA signal to remove low frequency tonic signals. The low frequency tonic signals have frequencies less than 0.05 Hz.

Step 410 includes subtracting the low frequency tonic signals and the EDA signals as generated in step 404.

Step 412 includes generating high frequency phasic signals. In an example, the high frequency phasic signals have frequencies greater than 0.05 Hz.

Figure 4B:
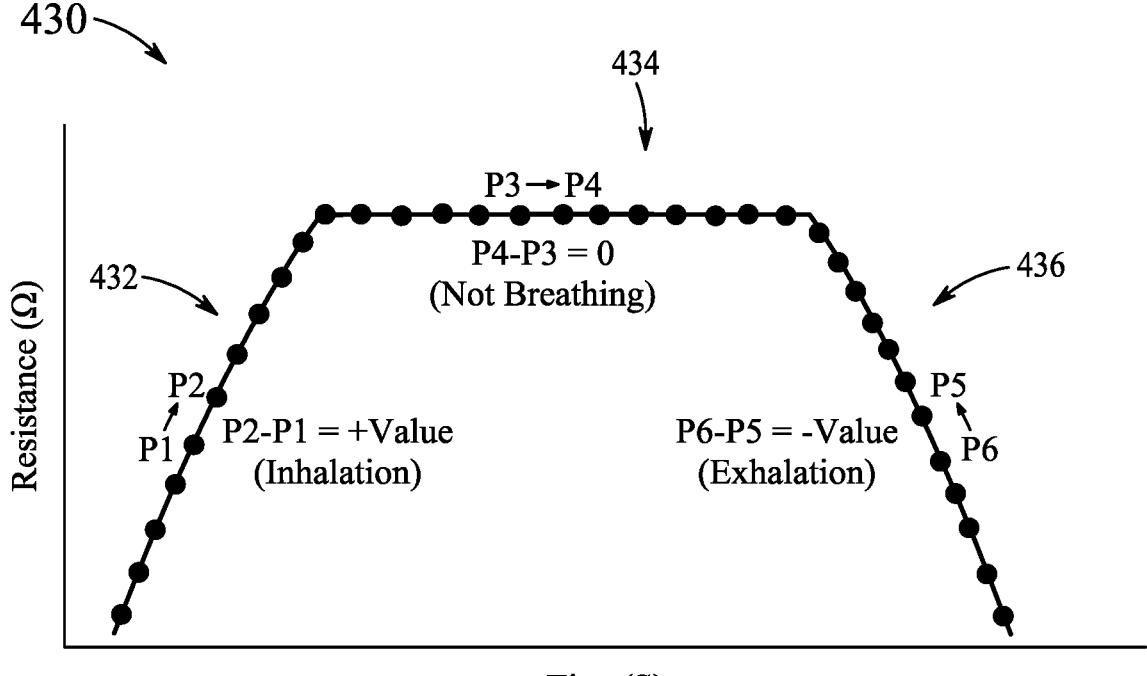
FIG. 4B is an exemplary flow chart of a respiration rate (RR) sensor, according to certain embodiments.

FIG. 4B is a respiratory rate detection algorithm 430 performed by the RR sensor 104. The wearable chest band 116 is secured around the chest of the patient. The wearable chest band 116 includes the wearable RR sensor 104.

In an example, the RR sensor 104 is configured to divide the chest movement into three phases: a first phase 432, a second phase 434, and a third phase 436.

During the first phase 432, as the patient inhales, the resistance of the wearable chest band 116 increases from P1 to P2, as shown in FIG. 4B.

During the second phase 434, when the patient does not breathe, there is no change in the resistance of the wearable chest band 116. As shown in FIG. 4B, P4–P3 is equal to zero.

During the third phase 436, when the patient exhales, the resistance of the wearable chest band 116 decreases from P5 to P6.

In an operative aspect, the RR sensor 104 is linear motion sensitive. Once the RR sensor 104 is placed around the chest of the patient, the RR sensor 104 measures the relative amount of expansion during respiration. The microcontroller 110 is configured to determine the amount of time required for the signal to change during various phases. For example, normal breathing takes between 3 and 5 seconds to complete each cycle (an inhalation cycle and an exhalation cycle). Each cycle has an increasing and decreasing value. If the period of the breathing cycle is shorter than 3 seconds, an abnormality in breathing known as tachypnea is indicated. On the other hand, if the signal does not change at all, it indicates that the breathing has stopped, which is referred to as apnea.

Figure 4C:
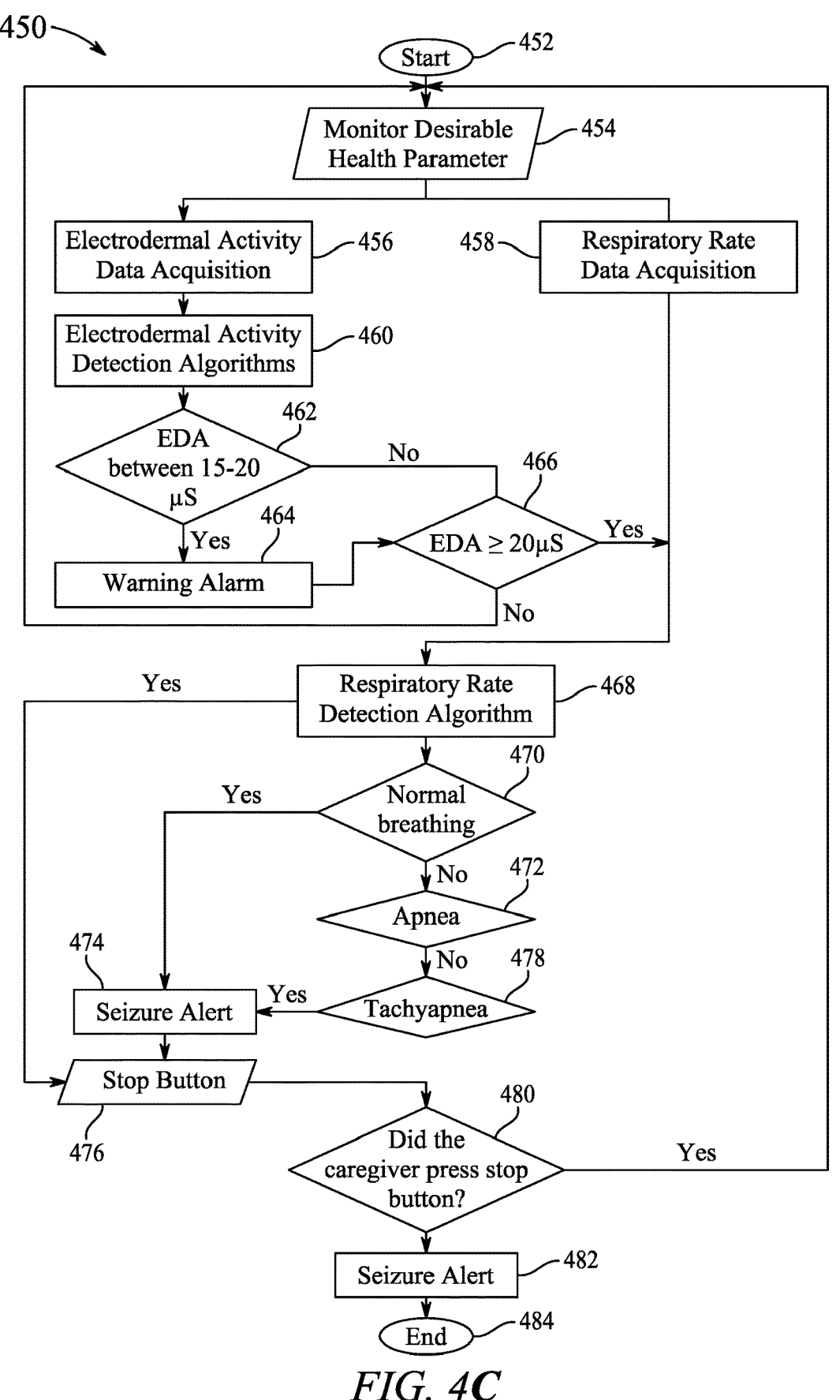
FIG. 4C is an exemplary flow chart of using an epi-seizure device, according to certain embodiments.

FIG. 4C is an exemplary flow chart 450 of the device (epi-seizure device) 100. The device 100 is worn by the patient.

Step 452 includes initialization of the device 100. The EDA sensor 102 is wrapped around the hand of the patient, such that the first nickel electrode contacts the medial phalange of the index finger, and the second nickel electrode contacts the medial phalange of the middle finger. Also, the wearable chest band 116, having the wearable RR sensor 104 is secured around the chest of the patient.

Step 454 includes monitoring the desirable health parameters of the patient using the epi-seizure device 100. The health parameters include the EDA and respiration rate of the patient.

Step 456 includes monitoring the electrodermal activity of the patient.

Step 458 includes monitoring the respiration rate of the patient.

Step 460 includes performing the electrodermal activity detection algorithm 400, as discussed in FIG. 4A.

Step 462 includes determining whether the amplitude (value) of the high-frequency phasic signals, as received by the microcontroller 110, lies between the first skin conductance threshold value (15 μSiemens) and the second skin conductance threshold value (20 μSiemens).

If the value of the high frequency phasic signals lies between the first skin conductance threshold value (15 μSiemens) and the second skin conductance threshold value (20 μSiemens), step 464 includes actuating, by the microcontroller 110, the alarm in the warning mode.

If the value of the high frequency phasic signals does not lie between the first skin conductance threshold value (15 μSiemens) and the second skin conductance threshold value (20 μSiemens), step 464 includes determining whether the amplitude (value) of the high-frequency phasic signals, as received by the microcontroller 110 is greater than or equal to the second skin conductance threshold value. If the amplitude of the high frequency phasic signals is greater than or equal to the second skin conductance threshold value, step 464 includes receiving the respiratory rate signals from the RR sensor 104. If the amplitude of the high frequency phasic signals is not greater than or equal to the second skin conductance threshold value, the EDA sensor 102 is configured to measure skin conductance and generate EDA signals.

Step 468 includes performing the respiratory rate detection algorithm 430, as discussed in FIG. 4B. Step 468 also includes calculating, by the microcontroller 110, a number of breaths per minute based on the respiratory rate signals.

Step 470 includes comparing, by the microcontroller 110, the number of breaths per minute to the first respiration rate threshold.

When the number of breaths per minute is less than the first respiration rate threshold, step 472 includes identifying, by the microcontroller 110, the apnea condition of the breathing and actuating the alarm in a seizure alert mode (as shown in step 474). In the apnea condition, the number of breaths per minute is less than 12 breaths per minute.

When the number of breaths per minute is greater than the first respiration rate threshold, step 476 includes comparing, by the microcontroller 110, the number of breaths per minute to the second respiration rate threshold. When the number of breaths per minute are greater than the second respiration rate threshold, step 476 includes identifying, by the microcontroller 110, the tachyapnea condition of the breathing and actuating the alarm in the seizure alert mode (as shown in step 474). In the tachyapnea condition, the number of breaths per minute is greater than 20 breaths per minute.

Step 478 includes pressing a stop button on the wearable chest band by a care giver after receiving the alarm.

Step 480 includes determining, by the microcontroller 110, whether the stop button on the wearable chest band 116 is pressed by the caregiver.

If the stop button is pressed by the caregiver, the device 100 is configured to follow the step 452 and onwards.

If the stop button is not pressed by the caregiver, step 482 includes actuating, by the microcontroller 110, the alarm in the seizure mode.

Step 484 includes disabling the device 100, when the patient putting down the EDA sensor 102 and the wearable chest band 116.

Figure 5A:
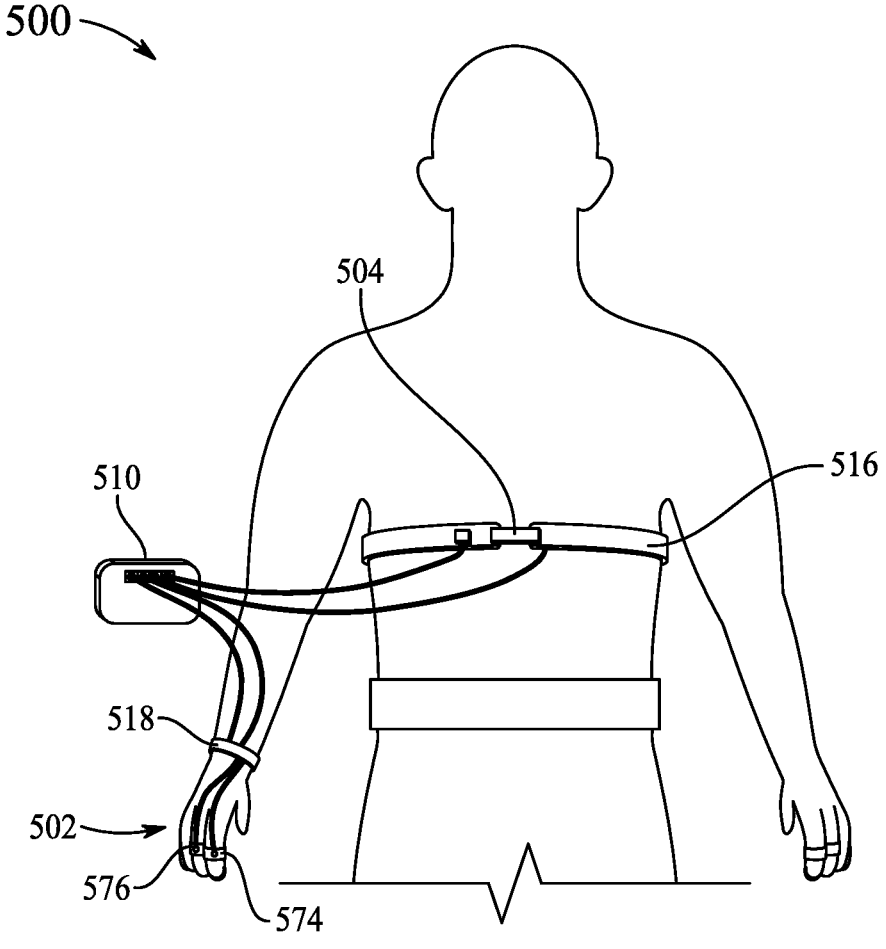
FIG. 5A is an exemplary illustration of a prototype of the epi-seizure device, according to certain embodiments.

FIG. 5A is an exemplary illustration of a prototype 500 of the epi-seizure device. As shown in FIG. 5A, the prototype 500 includes a wearable EDA sensor 502, a wearable RR sensor 504, a microcontroller 510, a wearable chest band 516, and a hand wrap 518. The microcontroller 510 is connected to the EDA sensor 502 and the RR sensor 504. In an example, the RR sensor 504 is a conductive rubber band. In an example, the conductive rubber band has a length of 14 cm and a width of 1.5 cm.

In an example, the microcontroller 510 has a length of 11 cm and a width of 7 cm. In an example, the wearable chest band 516 may have straps for adjustability and Velcro closure patches. For example, the wearable chest band 516 has a width of 5 cm.

The hand wrap 518 includes two nickel electrodes (574, 576). The first nickel electrode 574 is configured to contact the medial phalange of the index finger. The second nickel electrode 576 is configured to contact the medial phalange of the middle finger.

The basic construction and operation of the prototype 500 is similar to that of the device 100, and thus the construction and operation are not explained in detail for the sake of brevity.

Figure 5B:
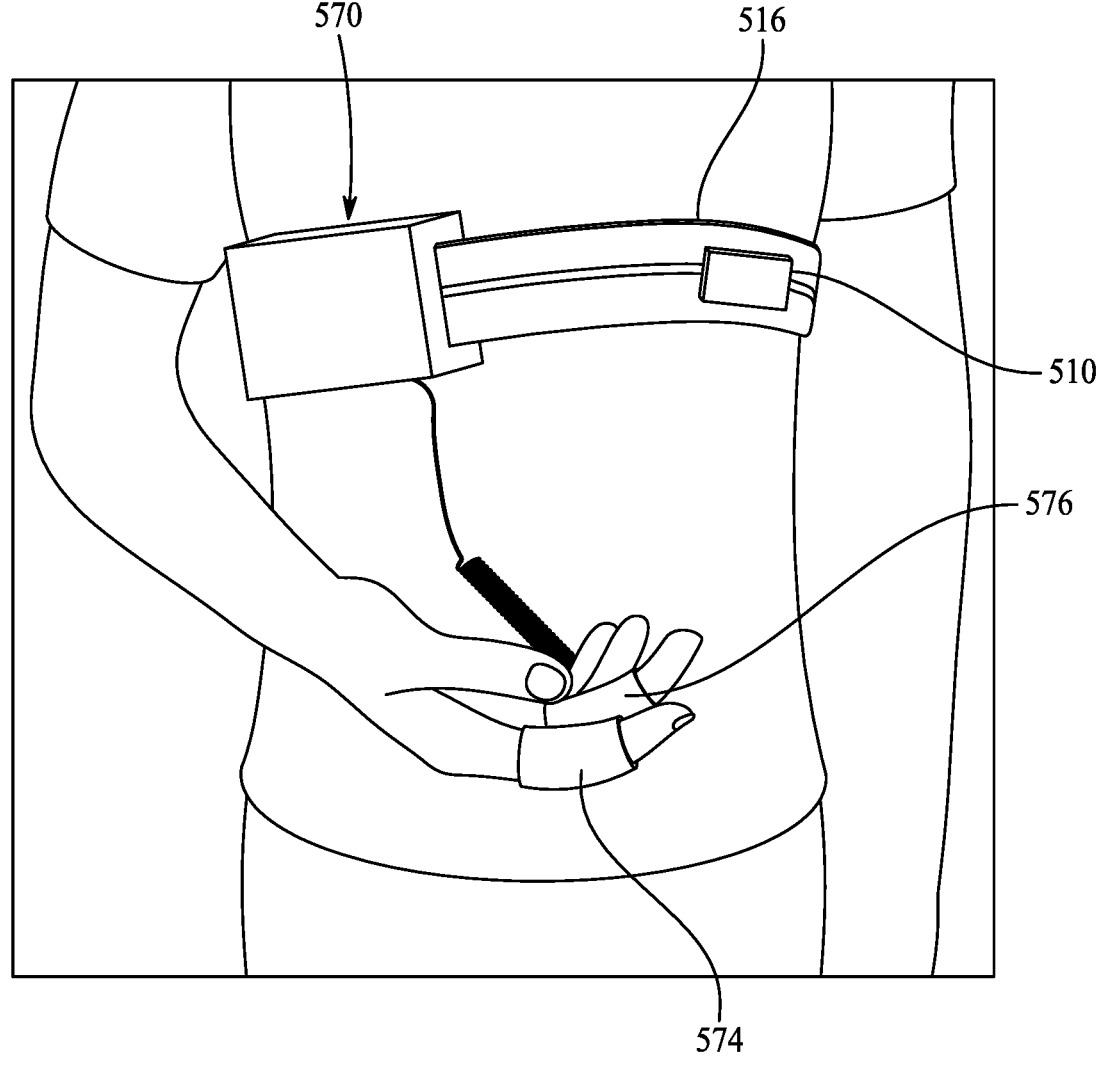
FIG. 5B demonstrates a person wearing the epi-seizure device, according to aspects of the present disclosure.

FIG. 5B demonstrates a person wearing the developed prototype (epi-seizure device). As shown in FIG. 5B, the microcontroller 510 may be placed in a housing 570. The housing 570 is configured to contain various components of the epi-seizure device. The housing 570 includes a battery, a plurality of connecting wires, and the microcontroller 510. In an example, the housing 570 is made of viscoelastic material, plastic, and like. The housing 570 may be attached to the wearable chest band 516 using a Velcro mechanism.

FIG. 6A-FIG. 6E represent user interfaces of the epi-seizure telemedicine application 142. In an example, the epi-seizure telemedicine application 142 is a mobile application executing on a Bluetooth enabled smart device 140. The epi-seizure telemedicine application 142 is configured to display any one of the warning alert, the seizure alert, and a "stop command" prompt on the display screen of the smart device 140. The epi-seizure telemedicine application 142 is configured to generate a plurality of pages on the display screen of the smart device 140. For example, the plurality of pages includes a home page, a registration page, a login page, a connection setup page, and a battery status page. The epi-seizure telemedicine application 142 is configured to detect any abnormality in the data received from the device 100 and provide the alarm after detection. However, if it turns out to be a false alarm, the caregiver can simply check on the patient's condition and then press on the stop button on the device 100 and on the screen on the smart device 140 displayed by the epi-seizure telemedicine application 142. For example, the stop button is represented by the sentence "THIS IS A FALSE ALARM! THE PATIENT IS OK!". In an example, the epi-seizure telemedicine application 142 was built in an Android application system using an Android Application Package (APK) file and uploaded on the cloud server. The cloud server is a logical server that is built, hosted and delivered through a cloud computing platform over the Internet. The cloud server possesses and exhibits similar capabilities and functionality to a typical server but are accessed remotely from a cloud service provider.

Figure 6A:
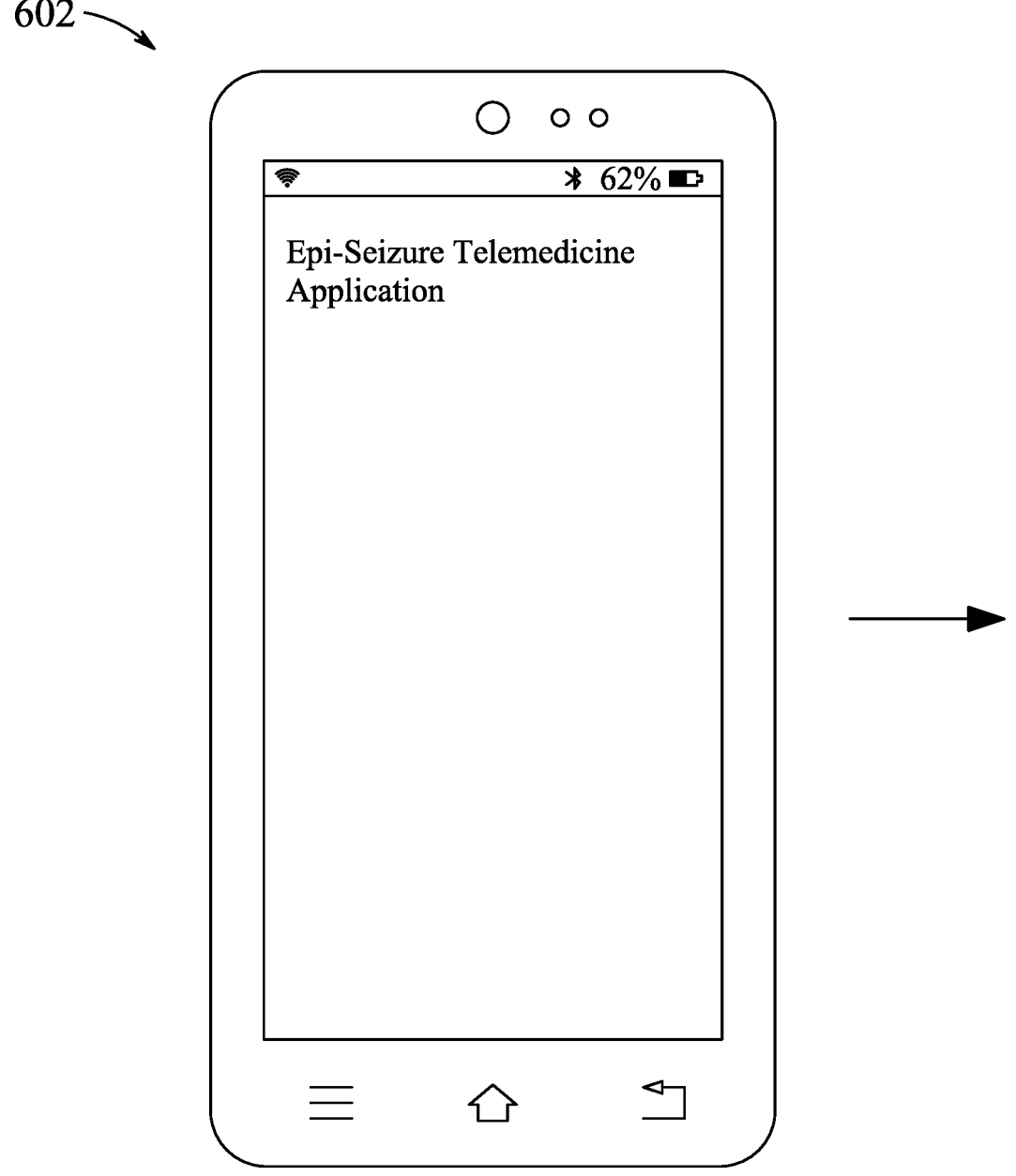
FIG. 6A is a user interface page showing an exemplary opening page for an epi-seizure telemedicine application, according to aspects of the present disclosure.

FIG. 6A represents an exemplary opening page 602 of the epi-seizure telemedicine application 142. The opening page 602 is configured to introduce the epi-seizure telemedicine application 142 to the user (caregiver). The opening page 602 informs the user what steps can be performed next and supports the user to explore many other pages. In an aspect, the opening page 602 represents an initial step of entering the epi-seizure telemedicine application 142 after installing the epi-seizure telemedicine application 142 from an application distribution platform. Examples of application distribution platforms include the App Store for iOS provided by Apple, Inc., Play Store for Android OS provided by Google Inc., and such application distribution platforms.

Figure 6B:
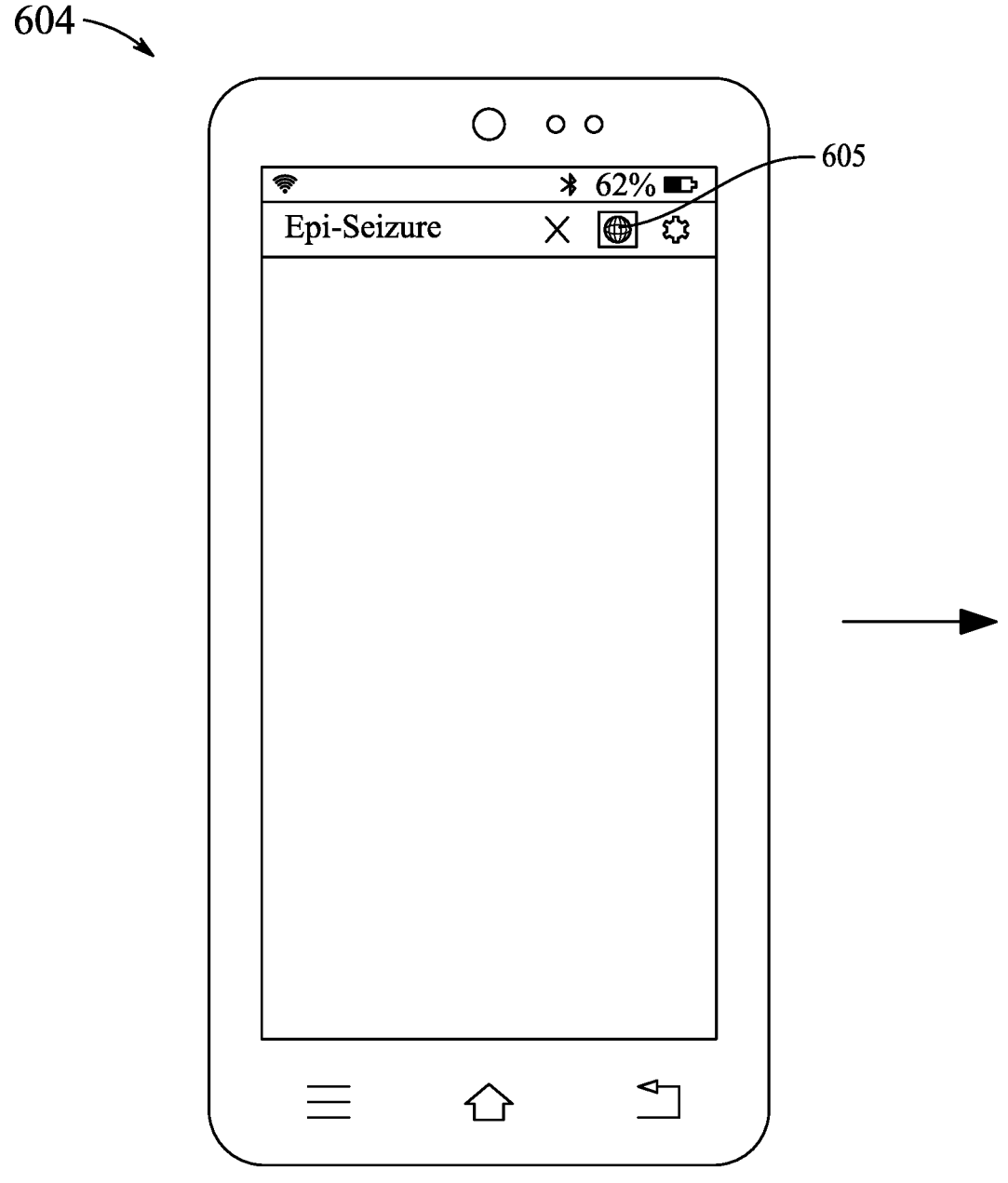
FIG. 6B is a user interface page illustrating a home page for the epi-seizure telemedicine application, according to aspects of the present disclosure.

FIG. 6B is a user interface page illustrating a home page 604 for the epi-seizure telemedicine application 142. For example, the home page 604 shows a directing circle (signup option) 605 that directs the user to a registration page after being clicked by the user.

Figure 6C:
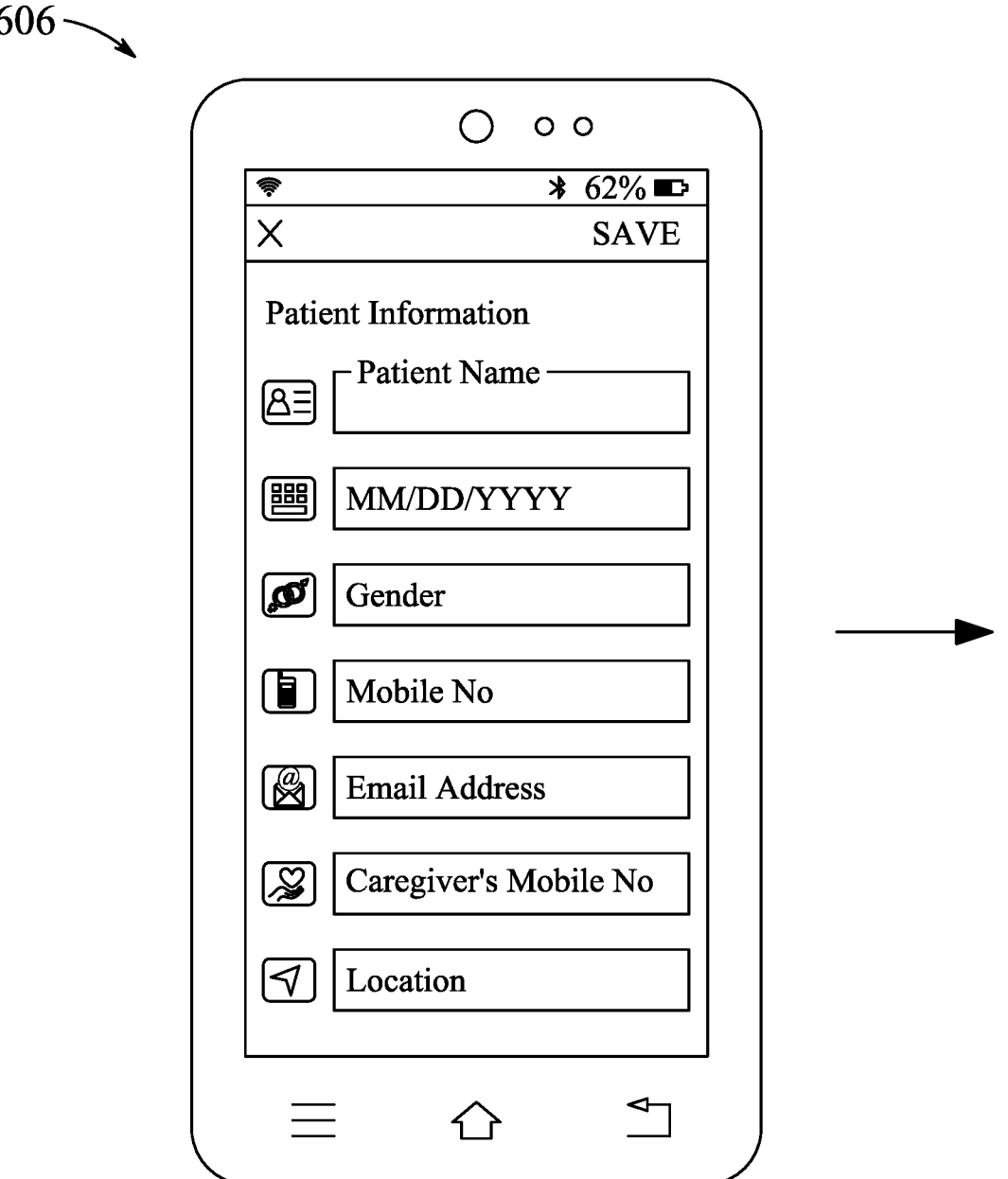
FIG. 6C is a user interface page illustrating a registration page for the epi-seizure telemedicine application, according to aspects of the present disclosure.

FIG. 6C illustrates a user interface page that shows the registration page 606 of the epi-seizure telemedicine application 142. The registration page 606 appears when the user initiates the epi-seizure telemedicine application 142 for registration. The registration page 606 prompts the user to create a profile. The registration page 606 includes options that prompt the user for information such as name of the patient, age of the patient, gender of the patient, address of the patient (not shown), email address of the patient, password, contact number of the patient, an emergency contact number (contact number of the caregiver), and like.

Figure 6D:
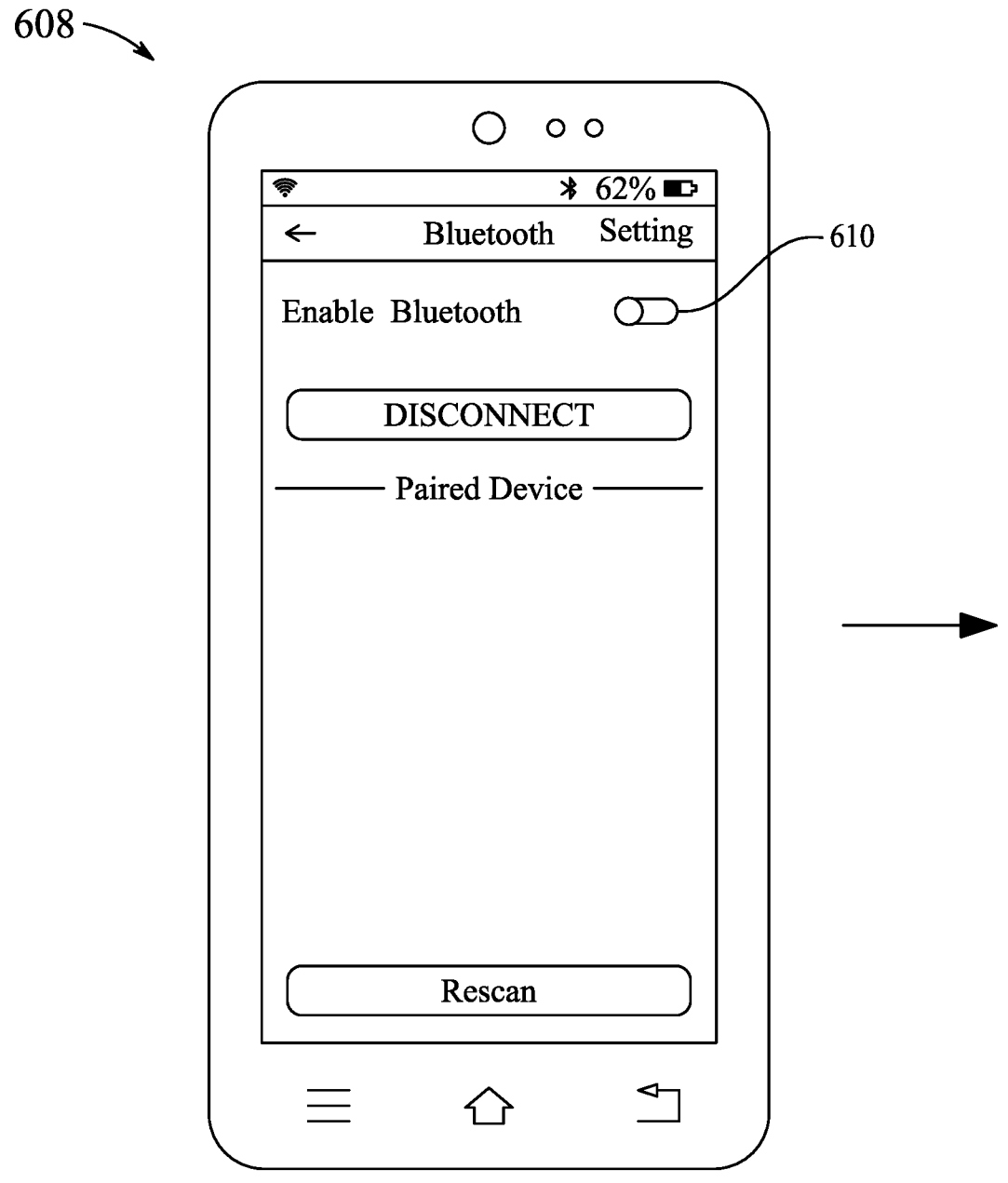
FIG. 6D is a user interface page illustrating a connection setup page of the epi-seizure telemedicine application, according to aspects of the present disclosure.

FIG. 6D is a user interface page illustrating a connection setup page 608 of the epi-seizure telemedicine application 142. As the user saves details in his/her profile, he/she will be directed to the connection setup page 608. As shown in FIG. 6D, the connection setup page 608 illustrates Bluetooth settings of the smart device 140.

The connection setup page 608 is a Bluetooth settings interface of the smart device 140. The Bluetooth setting interface includes functions such as a Bluetooth on/off control (as shown by 610) and a device name. After the smart device 140 detects an operation of tapping the control by the user, the smart device 140 may enable a Bluetooth function.

Referring to FIG. 6D, the Bluetooth settings interface may display paired devices and Available devices. A paired device may be a Bluetooth device previously connected to the smart device 140, and an available device may be a Bluetooth device found by the smart device 140.

Figure 6E:
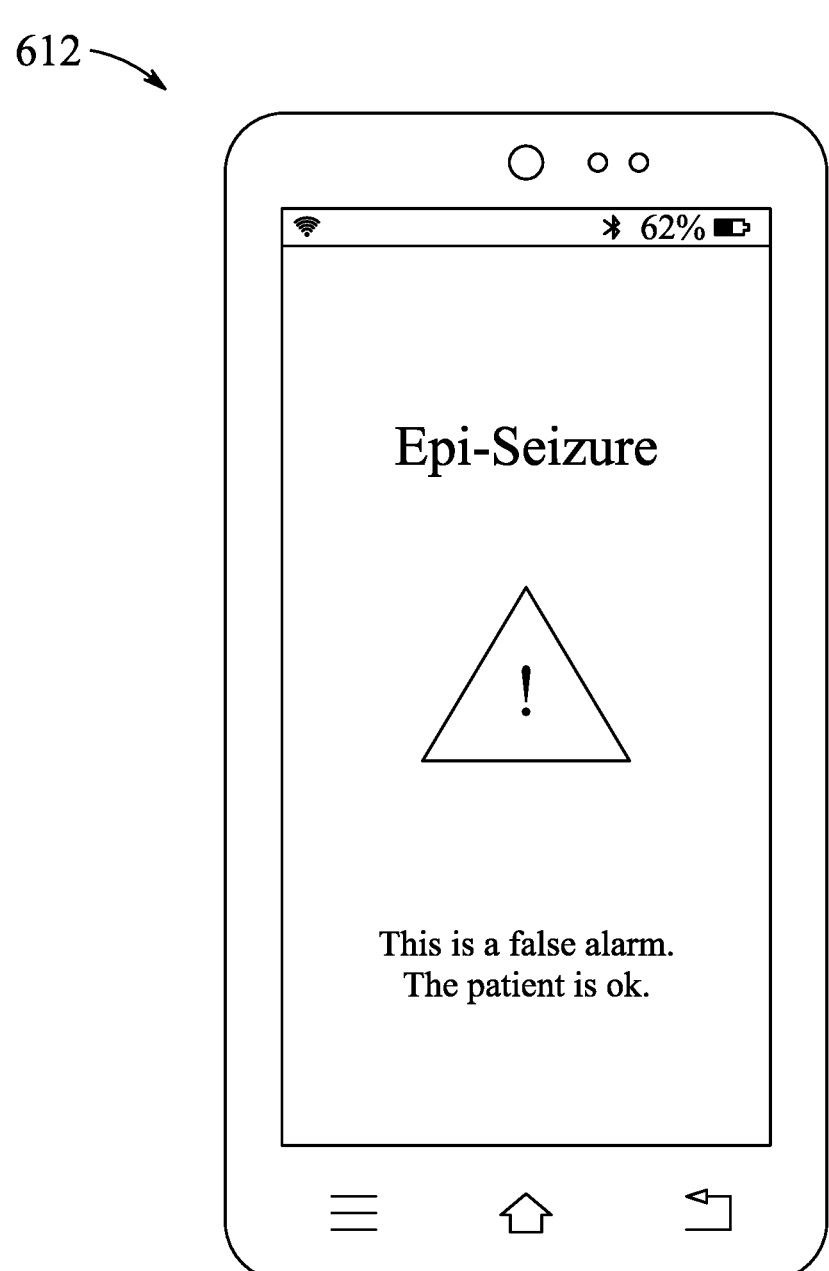
FIG. 6E is a user interface page showing a seizure alert generated by the epi-seizure telemedicine application, according to aspects of the present disclosure.

FIG. 6E is a user interface page showing a seizure alert 612 generated by the epi-seizure telemedicine application 142. After turning on the Bluetooth connection, the device 100 and the epi-seizure telemedicine application 142 are configured to communicate with each other. After establishing the connection with the smart device 140, the epi-seizure telemedicine application 142 receives the communications packet. The epi-seizure telemedicine application 142 is configured to extract the data from the received communications packet. The extracted data may include the low frequency tonic signals, the high frequency phasic signals, the number of breaths per minute, the warning alert, and the seizure alert. For example, if the extracted data has a warning alert, then the epi-seizure telemedicine application 142 displays the seizure alert 612 on the touchscreen of the smart device 140. In an example, the epi-seizure telemedicine application 142 is configured to display a prompt to press a stop command on a touchscreen of the smart device 140.

In some examples, the device 100 may be commutatively coupled to the smart device 140, and the device 100 may receive a plurality of information from the smart device 140.

In an operative aspect, the patient may register himself/herself with the device 100 or with the application in the smart device 140. During registration with the device 100 or the application in the smart device 140, the patient may be prompted to enter personal details (for example, name, mobile number, age, gender, etc.). In some examples, when the device 100 and the smart device 140 are used together, the device 100 may be configured and controlled using the application in the smart device 140. The smart device 140 is configured to receive the communications data from the device 100 after a predetermined time, thereby enhancing a battery life of the device 100. In another aspect, the smart device 140 is configured to receive the data from the device 100 in real-time.

The device 100 and/or the smart device 140 may be communicatively coupled to the cloud server periodically or continuously. The device 100 has a unique ID and may be linked with the cloud server. Similarly, the application in the smart device 140 may have a unique ID and may be linked with the cloud server.

The device 100 and/or the smart device 140 may be configured to upload sensor data to the cloud server for storing, processing or analysis.

The first embodiment is illustrated with respect to FIG. 1A-FIG. 1G. The first embodiment describes the device 100 for predicting and monitoring epileptic seizures. The device 100 includes a wearable electrodermal activity (EDA) sensor 102 configured to measure skin conductance and generate EDA signals, a wearable respiration rate (RR) sensor 104 configured to measure chest movement and generate respiratory rate signals, an alarm configured to have a warning mode and a seizure alert mode, a second order low pass filter having a cut-off frequency of 0.05 Hz, and a microcontroller 110. The second order low pass filter is configured to filter the EDA signals to remove low frequency tonic signals having frequencies less than 0.05 Hz and to pass high frequency phasic signals having frequencies greater than 0.05 Hz. The microcontroller 110 is connected to the second order low pass filter and the RR sensor 104, wherein the microcontroller 110 is configured to receive the high frequency phasic signals, compare an amplitude of the high frequency phasic signals to a first skin conductance threshold value and a second skin conductance threshold value, wherein the first skin conductance threshold is less than the second skin conductance threshold. When the amplitude of the high frequency phasic signals is greater than the first skin conductance threshold value but less than the second skin conductance threshold value, the microcontroller 110 is configured to actuate the alarm in the warning mode. When the amplitude of the high frequency phasic signals is greater than or equal to the second skin conductance threshold value, the microcontroller 110 is configured to receive the respiratory rate signals, calculate a number of breaths per minute based on the respiratory rate signals, and compare the number of breaths per minute to a first respiration rate threshold. When the number of breaths per minute is less than the first respiration rate threshold, the microcontroller 110 is configured to identify an apnea condition of the breathing and actuate the alarm in the seizure alert mode. When the number of breaths per minute is greater than the first respiration rate threshold, the microcontroller 110 is configured to compare the number of breaths per minute to a second respiration rate threshold. When the number of breaths per minute is greater than the second respiration rate threshold, the microcontroller 110 is configured to identify a tachyapnea condition of the breathing and actuate the alarm in the seizure alert mode.

In an aspect, the first skin conductance threshold value is 15 μSiemens and the second skin conductance threshold value is 20 μSiemens.

In an aspect, the first respiration rate threshold is 12 breaths per minute, and the second respiration rate threshold is 20 breaths per minute.

In an aspect, the device further includes a display screen 112 mounted on an exterior surface of the wearable RR sensor 104. The microcontroller 110 is further configured to identify abnormally high sweating indicative of a preictal stage of epileptic seizure when the high frequency phasic signals are greater than the first skin conductance threshold value of 15 μSiemens, identify apnea when the number of breaths per minute is less than 12 breaths per minute, identify normal breathing when the number of breaths per minute is between 12 breaths per minute and 20 breaths per minute, identify an emergency tachyapnea condition when the number of breaths per minute is greater than zero and less than 3 breaths per minute, and display any one of "Preictal Stage", "Ictal Stage", "Post Ictal Stage", "Apnea", "Normal Breathing", "Tachyapnea", "Warning" and "Seizure" on the display screen 112 based on the identification.

In an aspect, the microcontroller 110 is further configured to generate a communications packet including the low frequency tonic signals, the high frequency phasic signals, the number of breaths per minute, the warning alert and the seizure alert. The device further includes a communications device operatively connected to the microcontroller 110. The communications device is configured to transmit the communications packet to a smart device 140 configured with an epi-seizure telemedicine application 142. The epi-seizure telemedicine application 142 is configured to display any one of the warning alert, the seizure alert, and a prompt to press a stop command on a touchscreen of the smart device 140.

In an aspect, the device further includes a wearable chest band 116 configured to secure the wearable respiration rate sensor around a chest of a patient, and a hand wrap 118 configured to secure the EDA sensor 102 around a set of fingers of the patient.

In an aspect, the hand wrap 118 includes two nickel electrodes located so as to contact a medial phalange of each of an index finger and a middle finger.

In an aspect, the device further includes a rigid, rectangular plate 120 mounted to an exterior surface of the wearable chest band, a plurality of motion sensors 122 mounted around a perimeter of the rectangular plate 120, a rigid outer band 130 connected to the wearable chest band 116 so as to compress each motion sensor against the rigid, rectangular plate 120 as the chest rises, an attachment configured to hold the microcontroller 110 circuit on the wearable chest band 116 next to the rigid, rectangular plate 120, and a display screen 112 attached to the exterior surface of the wearable chest band. The motion sensors 122 are configured to provide the respiratory rate signals. The display screen 112 is connected to the microcontroller 110 circuit.

In an aspect, the motion sensors 122 include a pneumatic plunger 124 which rises and falls as a breath is inhaled and exhaled respectively, a magnet 126 attached to each pneumatic plunger 124, and a plurality of magnetic field sensors 128 attached to the rigid outer band 130. Each magnetic field sensor 128 is configured to sense a magnetic field generated by a respective magnet 126 and generate the respiratory rate signals in response to sensing the magnetic field.

In an aspect, the motion sensors 122 are selected from any one of linear motion sensors, strain sensors, hall sensors, capacitive sensors, pneumatic sensors and magnetic sensors.

In an aspect, the motion sensors 122 include a pneumatic plunger 124 which rises and falls as a breath is inhaled and exhaled, respectively, a conductive plate 134 attached to each pneumatic plunger 124, and a plurality of capacitive sensors attached to the rigid outer band 130. Each capacitive sensor is configured to sense changes in an electric field due to the proximity of each conductive plate 134 as the respective pneumatic plunger 124 rises and falls and generates respiratory rate signals in response to the changes in the electric field.

In an aspect, the microcontroller 110 is configured to predict a preictal stage of an epileptic seizure by monitoring the high frequency phasic signals, wherein the preictal stage is identified when the high frequency phasic signals are greater than the first skin conductance threshold value and less than the second skin conductance threshold value.

In an aspect, the microcontroller 110 is configured to identify an ictal stage of an epileptic seizure by monitoring the high frequency phasic signals and the breaths per minute. The ictal stage is identified when the high frequency phasic signals are greater than the second skin conductance threshold value and the breaths per minute are greater than 12 breaths per minute.

In an aspect, the microcontroller 110 is configured to identify a postictal stage of an epileptic seizure by monitoring the high frequency phasic signals and the breaths per minute. The postictal stage is identified when the high frequency phasic signals are less than the first skin conductance threshold value and the breaths per minute are less than 20 breaths per minute.

The second embodiment is illustrated with respect to FIG. 2. The second embodiment describes a system 200 for predicting and monitoring epileptic seizures. The system includes a wearable electrodermal activity (EDA) sensor 202, a wearable respiration rate (RR) sensor 204, an alarm 206, a second order low pass filter 208, a communications device 214, a smart device 240, and a microcontroller 210. The EDA sensor 202 is configured to measure skin conductance and generate EDA signals. The wearable respiration rate (RR) sensor is configured to measure chest movement and generate respiratory rate signals. The alarm is configured to have a warning mode and a seizure alert mode. The second order low pass filter has a cut-off frequency of 0.05 Hz. The second order low pass filter is configured to filter the EDA signals to remove low frequency tonic signals having frequencies less than 0.05 Hz and to pass high frequency phasic signals having frequencies greater than 0.05 Hz. The smart device 240 is configured with an epi-seizure telemedicine application 242. The microcontroller 210 connected to the communications device, the second order low pass filter and the RR sensor 204. The microcontroller 210 is configured to receive the high frequency phasic signals and compare an amplitude of the high frequency phasic signals to a first skin conductance threshold value and a second skin conductance threshold value, wherein the first skin conductance threshold is less than the second skin conductance threshold. When the amplitude of the high frequency phasic signals is greater than the first skin conductance threshold value but less than the second skin conductance threshold value, the microcontroller 210 is configured to actuate the alarm in the warning mode. When the amplitude of the high frequency phasic signals is greater than or equal to the second skin conductance threshold value, the microcontroller 210 is configured to receive the respiratory rate signals, calculate a number of breaths per minute based on the respiratory rate signals, and compare the number of breaths per minute to a first respiration rate threshold. When the number of breaths per minute is less than the first respiration rate threshold, the microcontroller 210 is configured to identify an apnea condition of the breathing and actuate the alarm in the seizure alert mode. When the number of breaths per minute is greater than the first respiration rate threshold, the microcontroller 210 is configured to compare the number of breaths per minute to a second respiration rate threshold. When the number of breaths per minute is greater than the second respiration rate threshold, the microcontroller 210 is configured to identify a tachyapnea condition of the breathing and actuate the alarm in the seizure alert mode. The microcontroller 210 is configured to generate a communications packet including the low frequency tonic signals, the high frequency phasic signals, the number of breaths per minute, the warning alert and the seizure alert, and transmit the packet to the smart device 240 configured with the epi-seizure telemedicine application 242. The epi-seizure application is configured to display any one of the warning alert, the seizure alert, and a prompt to press a stop command on a touchscreen of the smart device 240.

In an aspect, the communications device is configured to transmit the communications packet with a near field transceiver, and the smart device 240 is configured to receive the communications packet with a near field receiver.

In an aspect, the epi-seizure telemedicine application 242 is stored in a cloud server. The smart device 240 is registered with the epi-seizure telemedicine application 242 and stores an instance of the epi-seizure telemedicine application 242. The microcontroller 210 is registered with the instance of the epi-seizure telemedicine application 242 stored on the smart device 240.

In an aspect, the system includes a registration database 246 stored within the smart device 240 and operatively connected with the epi-seizure telemedicine application 242. The epi-seizure telemedicine application 242 is configured to display a prompt on the touchscreen of the smart device 240 requesting registration of the microcontroller 210 with the epi-seizure telemedicine application 242, register the microcontroller 210, and store the registration in the registration database 246.

The third embodiment is illustrated with respect to FIG. 1A-FIG. 6. The third embodiment describes a method of using an epi-seizure device. The method includes wrapping a wearable electrodermal activity (EDA) sensor including two nickel electrodes around a hand of a patient so that a first nickel electrode contacts a medial phalange of an index finger, and a second nickel electrode contacts a medial phalange of a middle finger. The method includes securing a wearable chest band 116 including wearable respiration rate sensor around a chest of a patient. The method includes turning on a microcontroller 110 of the wearable respiration rate sensor to start monitoring the patient for the onset of an epileptic seizure. The method includes measuring, by the wearable RR sensor 104, chest movement of the patient and generating respiratory rate signals. The method includes measuring, by the wearable EDA sensor 102, skin conductance of the patient and generating EDA signals. The method includes filtering, by a second order low pass filter having a cut-off frequency of 0.05 Hz, the EDA signals to remove low frequency tonic signals having frequencies less than 0.05 Hz and to pass high frequency phasic signals having frequencies greater than 0.05 Hz. The method includes receiving, by the microcontroller 110, the high frequency phasic signals and the respiratory rate signals. The method includes comparing, by the microcontroller 110, an amplitude of the high frequency phasic signals to a first skin conductance threshold value and a second skin conductance threshold value. The method includes actuating, by the microcontroller 110, an alarm in the warning mode when the amplitude of the high frequency phasic signals is greater than the first skin conductance threshold value but less than the second skin conductance threshold value. When the amplitude of the high frequency phasic signals is greater than or equal to the second skin conductance threshold value, the method includes calculating, by the microcontroller 110, a number of breaths per minute based on the respiratory rate signals. The method includes comparing, by the microcontroller 110, the number of breaths per minute to a first respiration rate threshold. When the number of breaths per minute is less than the first respiration rate threshold, the method includes identifying, by the microcontroller 110, an apnea condition of the breathing and actuating the alarm in a seizure alert mode. When the number of breaths per minute is greater than the first respiration rate threshold, the method includes comparing, by the microcontroller 110, the number of breaths per minute to a second respiration rate threshold. When the number of breaths per minute is greater than the second respiration rate threshold, the method includes identifying, by the microcontroller 110, a tachyapnea condition of the breathing and actuating the alarm in the seizure alert mode.

In an aspect, the method includes downloading an epi-seizure telemedicine application stored on a cloud server to a smart device and registering the microcontroller 110 with the epi-seizure telemedicine application 142 stored on a smart device 140. The method includes generating, by the microcontroller 110, a communications packet including the low frequency tonic signals, the high frequency phasic signals, the number of breaths per minute, the warning alert and the seizure alert. The method includes transmitting, by the microcontroller 110 over near field communications, the packet to the smart device 140 configured with the epi-seizure telemedicine application 142. The epi-seizure application is configured to display the any one of the warning alert, the seizure alert, and a prompt to press a stop command on a touchscreen of the smart device 140.

Figure 7:
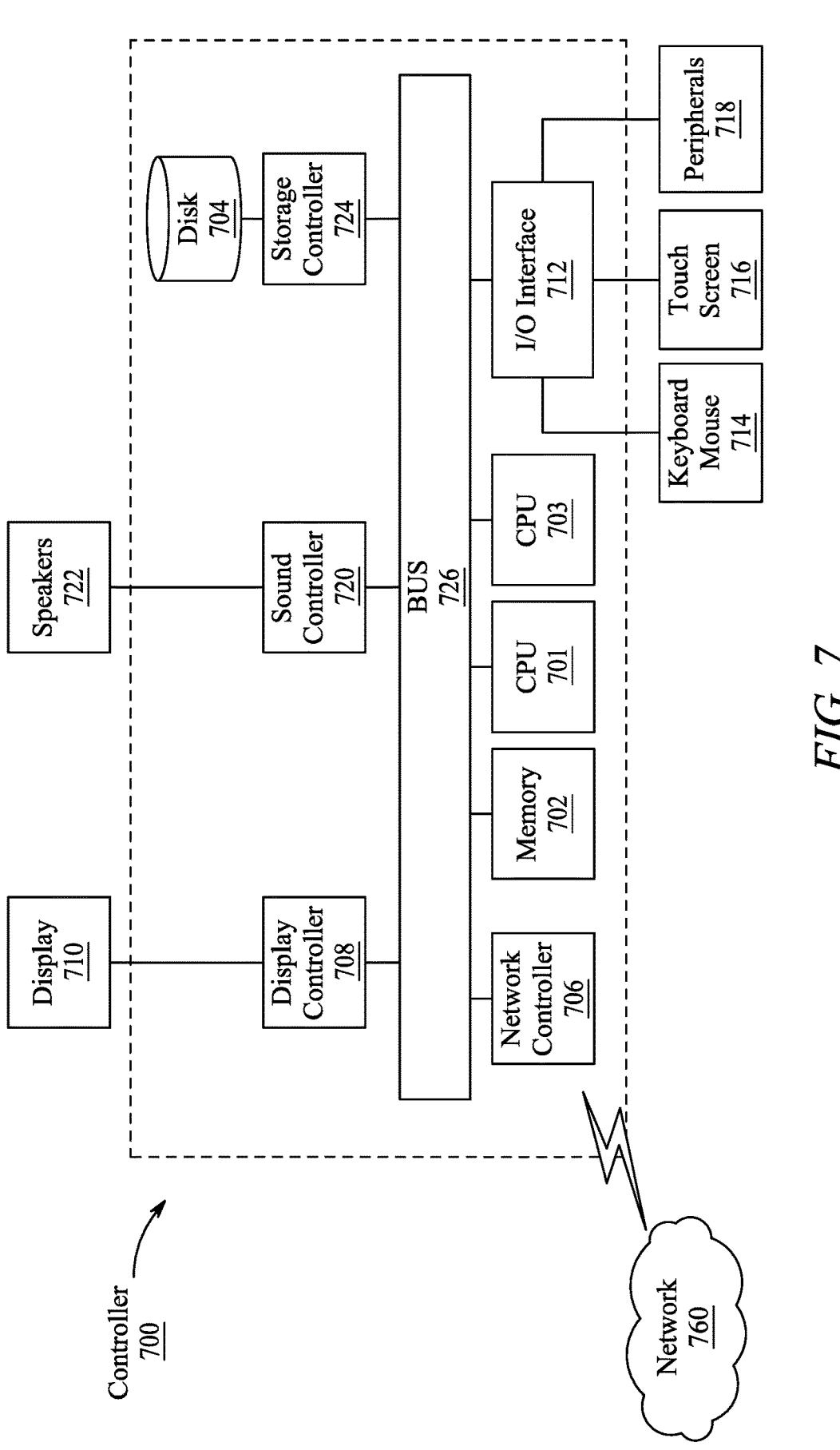
FIG. 7 is an illustration of a non-limiting example of details of computing hardware used in the computing system, according to certain embodiments.

Next, further details of the hardware description of the computing environment according to exemplary embodiments is described with reference to FIG. 7. In FIG. 7, a controller 700 is described is representative of the device 100 and the system 200 of FIG. 2 in which the microcontroller 110, 210 is a computing device which includes a CPU 701 which performs the processes described above/below. The process data and instructions may be stored in memory 702. These processes and instructions may also be stored on a storage medium disk 704 such as a hard drive (HDD) or portable storage medium or may be stored remotely.

The hardware elements in order to achieve the computing device may be realized by various circuitry elements, known to those skilled in the art. For example, CPU 701 or CPU 703 may be a Xenon or Core processor from Intel of America or an Opteron processor from AMD of America, or may be other processor types that would be recognized by one of ordinary skill in the art. Alternatively, the CPU 701, 703 may be implemented on an FPGA, ASIC, PLD or using discrete logic circuits, as one of ordinary skill in the art would recognize. Further, CPU 701, 703 may be implemented as multiple processors cooperatively working in parallel to perform the instructions of the inventive processes described above.

The computing device in FIG. 7 also includes a network controller 706, such as an Intel Ethernet PRO network interface card from Intel Corporation of America, for interfacing with network 760. As can be appreciated, the network 760 can be a public network, such as the Internet, or a private network such as an LAN or WAN network, or any combination thereof and can also include PSTN or ISDN sub-networks. The network 760 can also be wired, such as an Ethernet network, or can be wireless such as a cellular network including EDGE, 3G, 4G and 5G wireless cellular systems. The wireless network can also be WiFi, Bluetooth, or any other wireless form of communication that is known.

The computing device further includes a display controller 708, such as a NVIDIA GeForce GTX or Quadro graphics adaptor from NVIDIA Corporation of America for interfacing with display 710, such as a Hewlett Packard HPL2445w LCD monitor. A general purpose I/O interface 712 interfaces with a keyboard and/or mouse 714 as well as a touch screen panel 716 on or separate from display 710. General purpose I/O interface also connects to a variety of peripherals 718 including printers and scanners, such as an OfficeJet or DeskJet from Hewlett Packard.

A sound controller 720 is also provided in the computing device such as Sound Blaster X-Fi Titanium from Creative, to interface with speakers/microphone 722 thereby providing sounds and/or music.

The general purpose storage controller 724 connects the storage medium disk 704 with communication bus 726, which may be an ISA, EISA, VESA, PCI, or similar, for interconnecting all of the components of the computing device. A description of the general features and functionality of the display 710, keyboard and/or mouse 714, as well as the display controller 708, storage controller 724, network controller 706, sound controller 720, and general purpose I/O interface 712 is omitted herein for brevity as these features are known.

The exemplary circuit elements described in the context of the present disclosure may be replaced with other elements and structured differently than the examples provided herein.

Further, the claims are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the computing device communicates, such as a server or computer.

Further, the claims may be provided as a utility application, background daemon, or component of an operating system, or combination thereof, executing in conjunction with CPU 701, 703 and an operating system such as Microsoft Windows 7, Microsoft Windows 10, Microsoft Windows 11, UNIX, Solaris, LINUX, Apple MAC-OS and other systems known to those skilled in the art.

Figure 8:
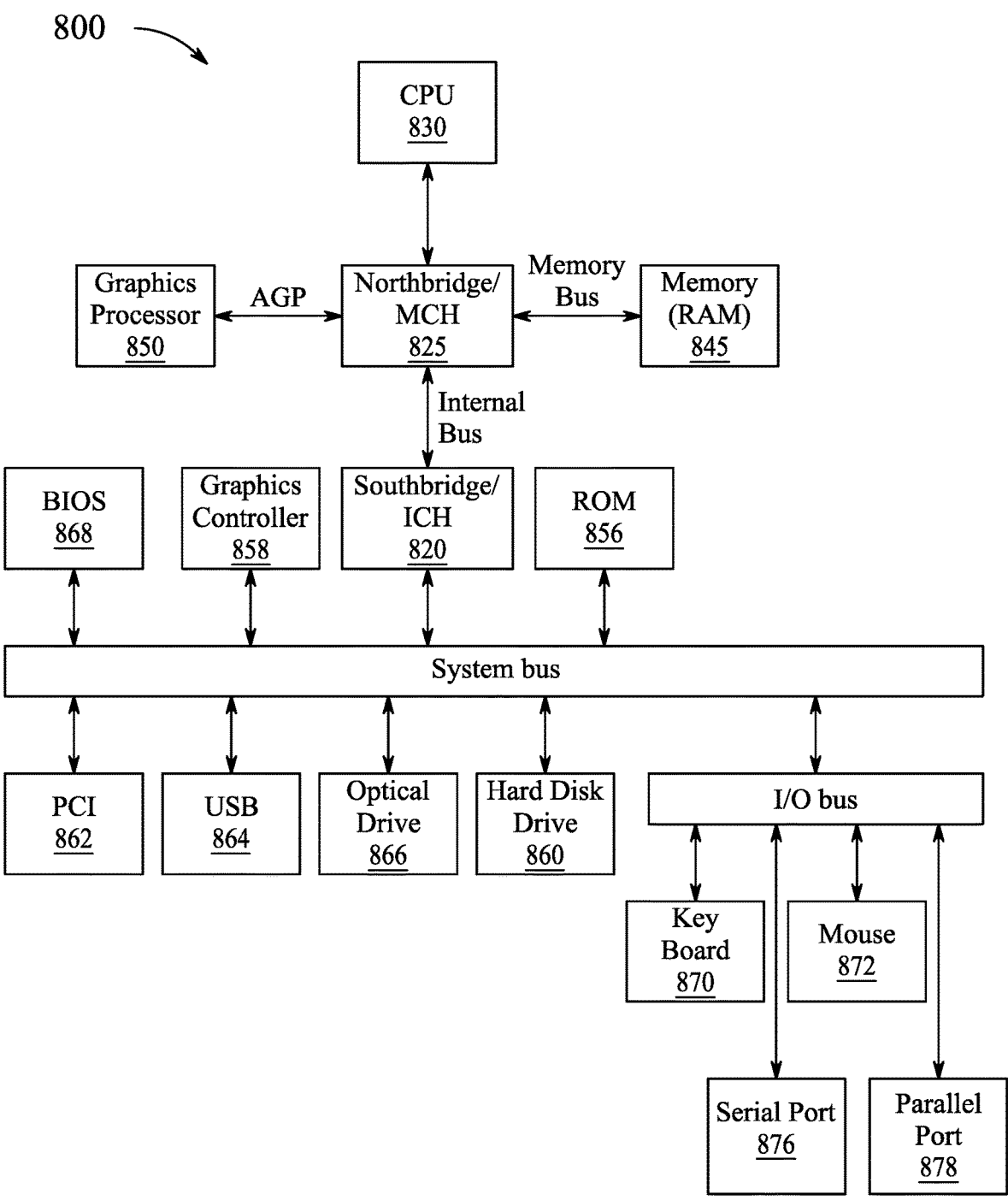
FIG. 8 is an exemplary schematic diagram of a data processing system used within the computing system, according to certain embodiments.

Moreover, circuitry configured to perform features described herein may be implemented in multiple circuit units (e.g., chips), or the features may be combined in circuitry on a single chipset, as shown on FIG. 8.

FIG. 8 shows a schematic diagram of a data processing system, according to certain embodiments, for performing the functions of the exemplary embodiments. The data processing system is an example of a computer in which code or instructions implementing the processes of the illustrative embodiments may be located.

In FIG. 8, data processing system 800 employs a hub architecture including a north bridge and memory controller hub (NB/MCH) 825 and a south bridge and input/output (I/O) controller hub (SB/ICH) 820. The central processing unit (CPU) 830 is connected to NB/MCH 825. The NB/MCH 825 also connects to the memory 845 via a memory bus, and connects to the graphics processor 850 via an accelerated graphics port (AGP). The NB/MCH 825 also connects to the SB/ICH 820 via an internal bus (e.g., a unified media interface or a direct media interface). The CPU Processing unit 830 may contain one or more processors and even may be implemented using one or more heterogeneous processor systems.

Figure 9:
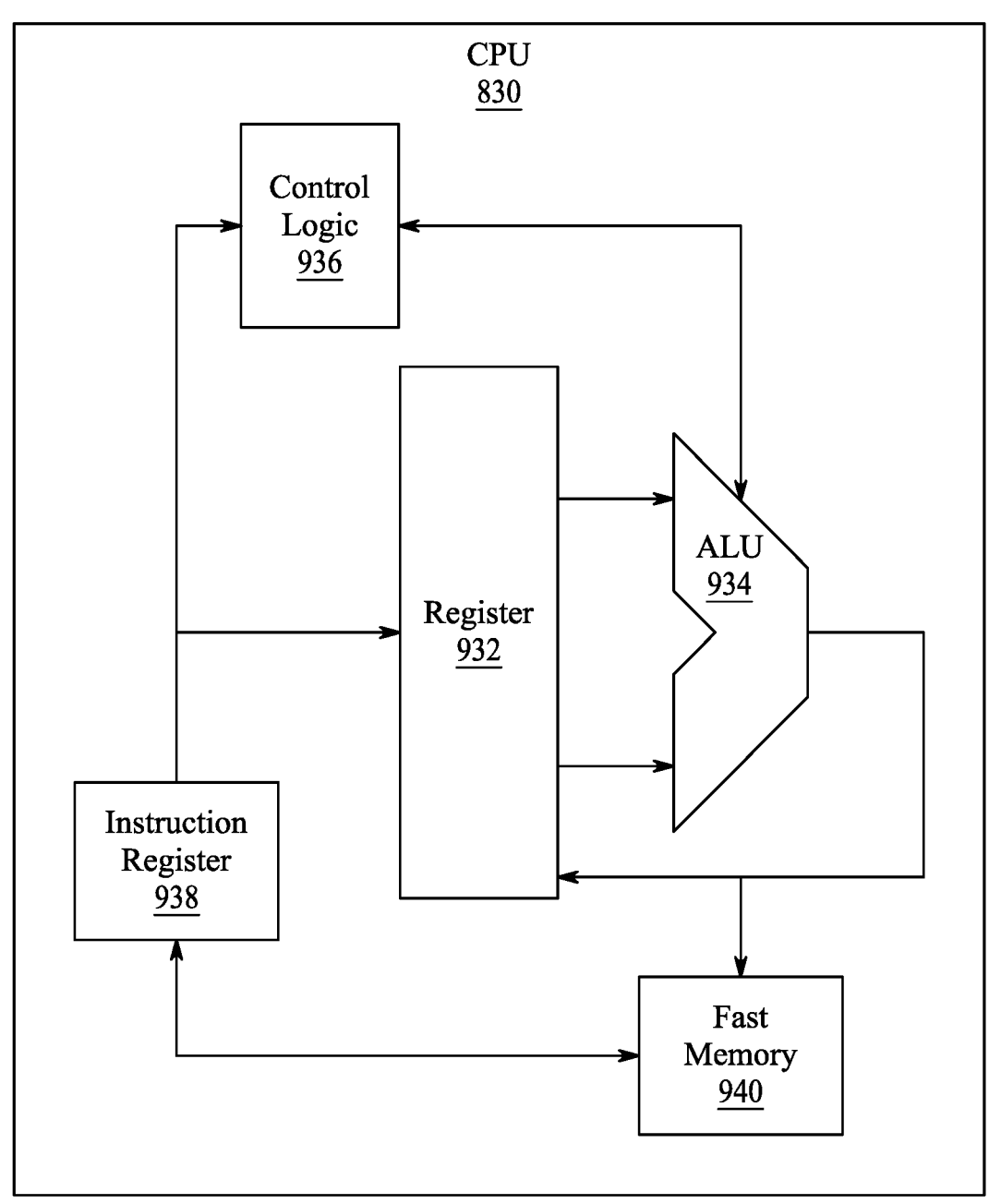
FIG. 9 is an exemplary schematic diagram of a processor used with the computing system, according to certain embodiments.

For example, FIG. 9 shows one implementation of CPU 830. In one implementation, the instruction register 938 retrieves instructions from the fast memory 940. At least part of these instructions are fetched from the instruction register 938 by the control logic 936 and interpreted according to the instruction set architecture of the CPU 830. Part of the instructions can also be directed to the register 932. In one implementation the instructions are decoded according to a hardwired method, and in another implementation the instructions are decoded according to a microprogram that translates instructions into sets of CPU configuration signals that are applied sequentially over multiple clock pulses. After fetching and decoding the instructions, the instructions are executed using the arithmetic logic unit (ALU) 934 that loads values from the register 932 and performs logical and mathematical operations on the loaded values according to the instructions. The results from these operations can be feedback into the register and/or stored in the fast memory 940. According to certain implementations, the instruction set architecture of the CPU 830 can use a reduced instruction set architecture, a complex instruction set architecture, a vector processor architecture, a very large instruction word architecture. Furthermore, the CPU 830 can be based on the Von Neuman model or the Harvard model. The CPU 830 can be a digital signal processor, an FPGA, an ASIC, a PLA, a PLD, or a CPLD. Further, the CPU 830 can be an x86 processor by Intel or by AMD; an ARM processor, a Power architecture processor by, e.g., IBM; a SPARC architecture processor by Sun Microsystems or by Oracle; or other known CPU architecture.

Referring again to FIG. 8, the data processing system 800 can include that the SB/ICH 820 is coupled through a system bus to an I/O Bus, a read only memory (ROM) 856, universal serial bus (USB) port 864, a flash binary input/output system (BIOS) 868, and a graphics controller 858. PCI/PCIe devices can also be coupled to SB/ICH 888 through a PCI bus 862.

The PCI devices may include, for example, Ethernet adapters, add-in cards, and PC cards for notebook computers. The Hard disk drive 860 and CD-ROM 866 can use, for example, an integrated drive electronics (IDE) or serial advanced technology attachment (SATA) interface. In one implementation the I/O bus can include a super I/O (SIO) device.

Further, the hard disk drive (HDD) 860 and optical drive 866 can also be coupled to the SB/ICH 820 through a system bus. In one implementation, a keyboard 870, a mouse 872, a parallel port 878, and a serial port 876 can be connected to the system bus through the I/O bus. Other peripherals and devices that can be connected to the SB/ICH 820 using a mass storage controller such as SATA or PATA, an Ethernet port, an ISA bus, a LPC bridge, SMBus, a DMA controller, and an Audio Codec.

Moreover, the present disclosure is not limited to the specific circuit elements described herein, nor is the present disclosure limited to the specific sizing and classification of these elements. For example, the skilled artisan will appreciate that the circuitry described herein may be adapted based on changes on battery sizing and chemistry, or based on the requirements of the intended back-up load to be powered.

Figure 10:
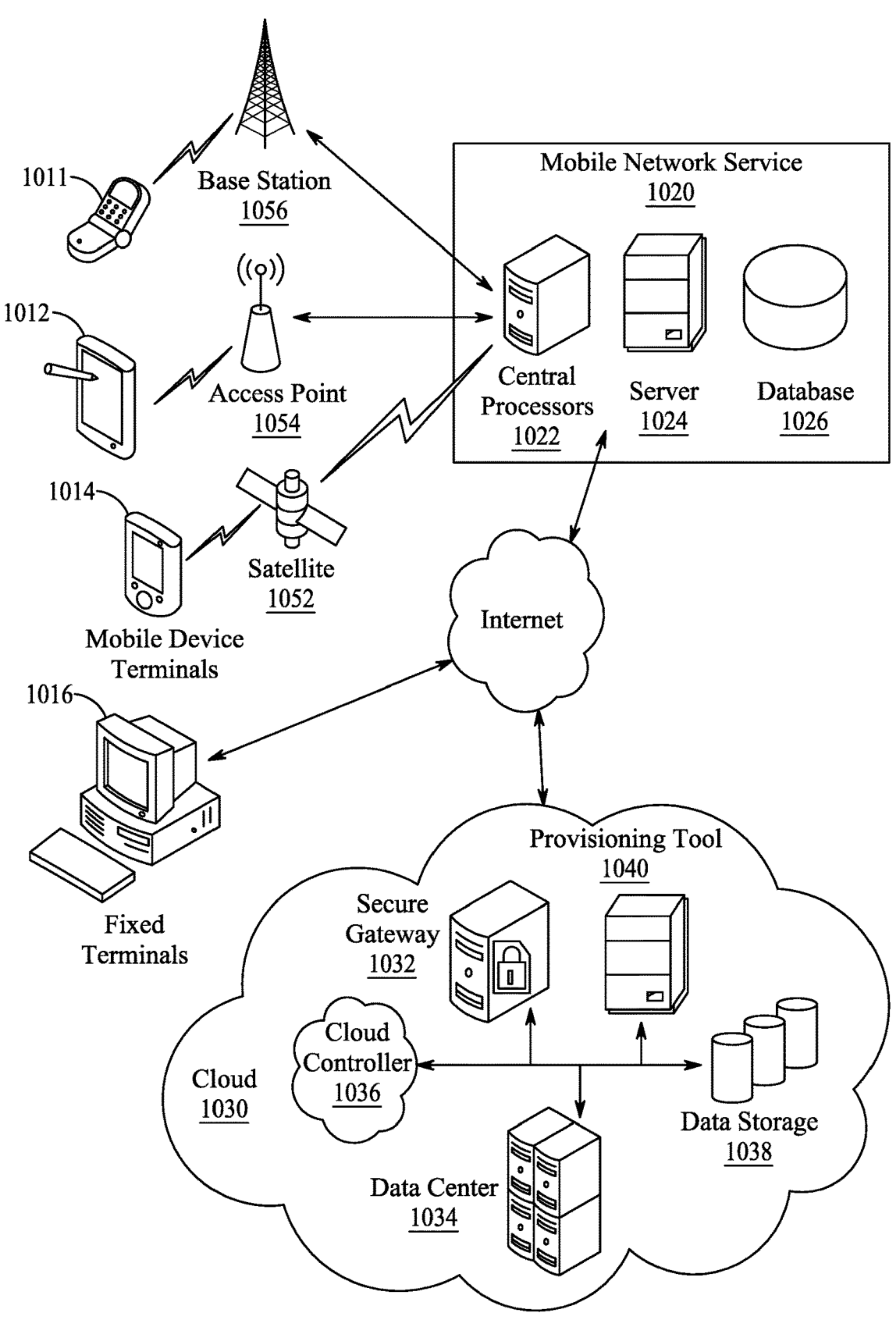
FIG. 10 is an illustration of a non-limiting example of distributed components which may share processing with the controller, according to certain embodiments.

The functions and features described herein may also be executed by various distributed components of a system. For example, one or more processors may execute these system functions, wherein the processors are distributed across multiple components communicating in a network. The distributed components may include one or more client and server machines, which may share processing, as shown by FIG. 10, in addition to various human interface and communication devices (e.g., display monitors, smart phones, tablets, personal digital assistants (PDAs)). More specifically, FIG. 10 illustrates client devices including smart phone 1011, tablet 1012, mobile device terminal 1014 and fixed terminals 1016. These client devices may be commutatively coupled with a mobile network service 1020 via base station 1056, access point 1054, satellite 1052 or via an internet connection. Mobile network service 1020 may comprise central processors 1022, server 1024 and database 1026. Fixed terminals 1016 and mobile network service 1020 may be commutatively coupled via an internet connection to functions in cloud 1030 that may comprise security gateway 1032, data center 1034, cloud controller 1036, data storage 1038 and provisioning tool 1040. The network may be a private network, such as a LAN or WAN, or may be a public network, such as the Internet. Input to the system may be received via direct user input and received remotely either in real-time or as a batch process. Additionally, some aspects of the present disclosures may be performed on modules or hardware not identical to those described. Accordingly, other aspects of the present disclosures are within the scope that may be claimed.

The above-described hardware description is a non-limiting example of corresponding structure for performing the functionality described herein.

Numerous modifications and variations of the present disclosure are possible in light of the above teachings. It is therefore to be understood that within the scope of the appended claims, the invention may be practiced otherwise than as specifically described herein.

The invention claimed is:

1. A device for predicting and monitoring epileptic seizures, comprising:
   a wearable electrodermal activity (EDA) sensor configured to measure skin conductance and generate EDA signals;
   a wearable respiration rate (RR) sensor configured to measure chest movement and generate respiratory rate signals;
   an alarm configured to have a warning mode and a seizure alert mode;
   a second order low pass filter having a cut-off frequency of 0.05 Hz, wherein the second order low pass filter is configured to filter the EDA signals to remove low frequency tonic signals having frequencies less than 0.05 Hz and to pass high frequency phasic signals having frequencies greater than 0.05 Hz;

a microcontroller connected to the second order low pass filter and the RR sensor, wherein the microcontroller is configured to:

receive the high frequency phasic signals;

compare an amplitude of the high frequency phasic signals to a first skin conductance threshold value and a second skin conductance threshold value, wherein the first skin conductance threshold is less than the second skin conductance threshold;

when the amplitude of the high frequency phasic signals is greater than the first skin conductance threshold value but less than the second skin conductance threshold value, actuate the alarm in the warning mode;

when the amplitude of the high frequency phasic signals is greater than or equal to the second skin conductance threshold value:

receive the respiratory rate signals;

calculate a number of breaths per minute based on the respiratory rate signals;

compare the number of breaths per minute to a first respiration rate threshold;

when the number of breaths per minute is less than the first respiration rate threshold, identify an apnea condition of the breathing and actuate the alarm in the seizure alert mode;

when the number of breaths per minute is greater than the first respiration rate threshold, compare the number of breaths per minute to a second respiration rate threshold; and when the number of breaths per minute is greater than the second respiration rate threshold, identify a tachyapnea condition of the breathing and actuate the alarm in the seizure alert mode.

2. The device of claim 1, wherein first skin conductance threshold value is 15 μSiemens and the second skin conductance threshold value is 20 μSiemens.

3. The device of claim 2, wherein:

the first respiration rate threshold is 12 breaths per minute; and the second respiration rate threshold is 20 breaths per minute.

4. The device of claim 3, further comprising:

a display screen mounted on an exterior surface of the wearable RR sensor;

wherein the microcontroller is further configured to:

identify abnormally high sweating indicative of a preictal stage of epileptic seizure when the high frequency phasic signals are greater than the first skin conductance threshold value of 15 μSiemens;

identify apnea when the number of breaths per minute is less than 12 breaths per minute;

identify normal breathing when the number of breaths per minute is between 12 breaths per minute and 20 breaths per minute;

identify an emergency tachyapnea condition when the number of breaths per minute is greater than zero and less than 3 breaths per minute; and display any one of "Preictal Stage", "Ictal Stage", "Post Ictal Stage", "Apnea", "Normal Breathing", "Tachyapnea", "Warning" and "Seizure" on the display screen based on the identification.

5. The device of claim 1, further comprising:

the microcontroller is further configured to generate a communications packet including the low frequency tonic signals, the high frequency phasic signals, the number of breaths per minute, the warning alert and the seizure alert; and a communications device operatively connected to the microcontroller, wherein the communications device is configured to transmit the communications packet to a smart device configured with an epi-seizure telemedicine application, wherein the epi-seizure telemedicine application is configured to display any one of the warning alert, the seizure alert, and a prompt to press a stop command on a touchscreen of the smart device.

6. The device of claim 1, further comprising:

a wearable chest band configured to secure the wearable respiration rate sensor around a chest of a patient; and a hand wrap configured to secure the EDA sensor around a set of fingers of the patient.

7. The device of claim 6, wherein the hand wrap includes two nickel electrodes located so as to contact a medial phalange of each of an index finger and a middle finger.

8. The device of claim 6, further comprising:

a rigid, rectangular plate mounted to an exterior surface of the wearable chest band;

a plurality of motion sensors mounted around a perimeter of the rectangular plate;

a rigid outer band connected to the wearable chest band so as to compress each motion sensor against the rigid, rectangular plate as the chest rises, wherein the motion sensors are configured to provide the respiratory rate signals;

an attachment configured to hold the microcontroller circuit on the wearable chest band next to the rigid, rectangular plate; and a display screen attached to the exterior surface of the wearable chest band, wherein the display screen is connected to the microcontroller circuit.

9. The device of claim 8, wherein the motion sensors comprise a pneumatic plunger which rises and falls as a breath is inhaled and exhaled respectively;

a magnet attached to each pneumatic plunger; and a plurality of magnetic field sensors attached to the rigid outer band, wherein each magnetic field sensor is configured to sense a magnetic field generated by a respective magnet and generate the respiratory rate signals in response to sensing the magnetic field.

10. The device of claim 8, wherein the motion sensors are selected from any one of linear motion sensors, linearly sliding potentiometers, strain sensors, capacitive sensors, hall sensors, pneumatic sensors and magnetic sensors.

11. The device of claim 8, wherein the motion sensors comprise:

a pneumatic plunger which rises and falls as a breath is inhaled and exhaled respectively;

a conductive plate attached to each pneumatic plunger; and a plurality of capacitive sensors attached to the rigid outer band, wherein each capacitive sensor is configured to sense changes in an electric field due to the proximity of each conductive plate as the respective pneumatic plunger rises and falls and generate respiratory rate signals in response to the changes in the electric field.

12. The device of claim 1, wherein the microcontroller is configured to:

predict a preictal stage of an epileptic seizure by monitoring the high frequency phasic signals, wherein the preictal stage is identified when the high frequency phasic signals are greater than the first skin conductance threshold value and less than the second skin conductance threshold value.

13. The device of claim 1, wherein the microcontroller is configured to:

identify an ictal stage of an epileptic seizure by monitoring the high frequency phasic signals and the breaths per minute, wherein the ictal stage is identified when the high frequency phasic signals are greater than the second skin conductance threshold value and the breaths per minute are greater than 12 breaths per minute.

14. The device of claim 1, wherein the microcontroller is configured to:

identify a postictal stage of an epileptic seizure by monitoring the high frequency phasic signals and the breaths per minute, wherein the postictal stage is identified when the high frequency phasic signals are less than the first skin conductance threshold value and the breaths per minute are less than 20 breaths per minute.

15. A system for predicting and monitoring epileptic seizures, comprising:

a wearable electrodermal activity (EDA) sensor configured to measure skin conductance and generate EDA signals;

a wearable respiration rate (RR) sensor configured to measure chest movement and generate respiratory rate signals;

an alarm configured to have a warning mode and a seizure alert mode;

a second order low pass filter having a cut-off frequency of 0.05 Hz, wherein the second order low pass filter is configured to filter the EDA signals to remove low frequency tonic signals having frequencies less than 0.05 Hz and to pass high frequency phasic signals having frequencies greater than 0.05 Hz;

a communications device;

a smart device configured with an epi-seizure telemedicine application;

a microcontroller connected to the communications device, the second order low pass filter and the RR sensor, wherein the microcontroller is configured to:

receive the high frequency phasic signals;

compare an amplitude of the high frequency phasic signals to a first skin conductance threshold value and a second skin conductance threshold value, wherein the first skin conductance threshold is less than the second skin conductance threshold;

when the amplitude of the high frequency phasic signals is greater than the first skin conductance threshold value but less than the second skin conductance threshold value, actuate the alarm in the warning mode;

when the amplitude of the high frequency phasic signals is greater than or equal to the second skin conductance threshold value:

receive the respiratory rate signals;

calculate a number of breaths per minute based on the respiratory rate signals;

compare the number of breaths per minute to a first respiration rate threshold;

when the number of breaths per minute is less than the first respiration rate threshold, identify an apnea condition of the breathing and actuate the alarm in the seizure alert mode;

when the number of breaths per minute is greater than the first respiration rate threshold, compare the number of breaths per minute to a second respiration rate threshold;

36 when the number of breaths per minute is greater than the second respiration rate threshold, identify a tachyapnea condition of the breathing and actuate the alarm in the seizure alert mode;

generate a communications packet including the low frequency tonic signals, the high frequency phasic signals, the number of breaths per minute, the warning alert and the seizure alert; and transmit the packet to the smart device configured with the epi-seizure telemedicine application, wherein the epi-seizure application is configured to display the any one of the warning alert, the seizure alert, and a prompt to press a stop command on a touchscreen of the smart device.

16. The system of claim 15, wherein:

the communications device is configured to transmit the communications packet with a near field transceiver, and the smart device is configured to receive the communications packet with a near field receiver.

17. The system of claim 15, wherein:

the epi-seizure telemedicine application is stored in a cloud server;

the smart device is registered with the epi-seizure telemedicine application and stores an instance of the epi-seizure telemedicine application; and the microcontroller is registered with the instance of the epi-seizure telemedicine application stored on the smart device.

18. The system of claim 17, further comprising:

a registration database stored within the smart device and operatively connected with the epi-seizure telemedicine application;

wherein the epi-seizure telemedicine application is configured to:

display a prompt on the touchscreen of the smart device requesting registration of the microcontroller with the epi-seizure telemedicine application;

register the microcontroller; and store the registration in the registration database.

19. A method of using an epi-seizure device, comprising:

wrapping a wearable electrodermal activity (EDA) sensor including two nickel electrodes around a hand of a patient so that a first nickel electrode contacts a medial phalange of an index finger, and a second nickel electrode contacts a medial phalange of a middle finger;

securing a wearable chest band including wearable respiration rate sensor around a chest of a patient;

turning on a microcontroller of the wearable respiration rate sensor to start monitoring the patient for the onset of an epileptic seizure;

measuring, by the wearable RR sensor, chest movement of the patient and generating respiratory rate signals;

measuring, by the wearable EDA sensor, a skin conductance of the patient and generating EDA signals;

filtering, by a second order low pass filter having a cut-off frequency of 0.05 Hz, the EDA signals to remove low frequency tonic signals having frequencies less than 0.05 Hz and to pass high frequency phasic signals having frequencies greater than 0.05 Hz;

receiving, by the microcontroller, the high frequency phasic signals and the respiratory rate signals;

comparing, by the microcontroller, an amplitude of the high frequency phasic signals to a first skin conductance threshold value and a second skin conductance threshold value;

actuating, by the microcontroller, an alarm in the warning mode when the amplitude of the high frequency phasic signals is greater than the first skin conductance threshold value but less than the second skin conductance threshold value;

when the amplitude of the high frequency phasic signals is greater than or equal to the second skin conductance threshold value, calculating, by the microcontroller, a number of breaths per minute based on the respiratory rate signals;

comparing, by the microcontroller, the number of breaths per minute to a first respiration rate threshold;

when the number of breaths per minute is less than the first respiration rate threshold, identifying, by the microcontroller, an apnea condition of the breathing and actuating the alarm in a seizure alert mode;

when the number of breaths per minute is greater than the first respiration rate threshold, comparing, by the microcontroller, the number of breaths per minute to a second respiration rate threshold; and when the number of breaths per minute is greater than the second respiration rate threshold, identifying, by the microcontroller, a tachyapnea condition of the breathing and actuating the alarm in the seizure alert mode.

20. The method of claim 19, further comprising:

downloading an epi-seizure telemedicine application stored on a cloud server to a smart device;

registering the microcontroller with the epi-seizure telemedicine application;

generating, by the microcontroller, a communications packet including the low frequency tonic signals, the high frequency phasic signals, the number of breaths per minute, the warning alert and the seizure alert; and transmitting, by the microcontroller, over near field communications, the packet to the smart device configured with the epi-seizure telemedicine application, wherein the epi-seizure application is configured to display any one of the warning alert, the seizure alert, and a prompt to press a stop command on a touchscreen of the smart device.

* * * * *